United States Patent
Masuda

(10) Patent No.: US 8,787,782 B2
(45) Date of Patent: Jul. 22, 2014

(54) TONER-DENSITY CALCULATING METHOD, REFLECTIVE OPTICAL SENSOR, REFLECTIVE OPTICAL SENSOR DEVICE, AND IMAGE FORMING APPARATUS

(71) Applicant: Koji Masuda, Kanagawa (JP)

(72) Inventor: Koji Masuda, Kanagawa (JP)

(73) Assignee: Ricoh Company, Ltd., Tokyo (JP)

( * ) Notice: Subject to any disclaimer, the term of this patent is extended or adjusted under 35 U.S.C. 154(b) by 0 days.

(21) Appl. No.: 14/032,670

(22) Filed: Sep. 20, 2013

(65) Prior Publication Data
US 2014/0023391 A1 Jan. 23, 2014

Related U.S. Application Data

(60) Division of application No. 13/539,511, filed on Jul. 2, 2012, now Pat. No. 8,564,782, and a continuation of application No. 12/399,356, filed on Mar. 6, 2009, now Pat. No. 8,260,164.

(30) Foreign Application Priority Data

Mar. 18, 2008 (JP) .................... 2008-070198
Sep. 17, 2008 (JP) .................... 2008-238451

(51) Int. Cl.
*G03G 15/00* (2006.01)
(52) U.S. Cl.
CPC ........ *G03G 15/5041* (2013.01); *G03G 15/5058* (2013.01)
USPC .................................................. 399/49
(58) Field of Classification Search
CPC .......... G03G 15/5058; G03G 15/5041; G03G 15/5062
See application file for complete search history.

(56) References Cited

U.S. PATENT DOCUMENTS

| | | |
|---|---|---|
| 5,839,016 A | 11/1998 | Folkins et al. |
| 5,875,051 A | 2/1999 | Suzuki et al. |
| 5,909,235 A | 6/1999 | Folkins |
| 6,069,724 A | 5/2000 | Hayashi et al. |
| 6,075,638 A | 6/2000 | Masuda |
| 6,081,386 A | 6/2000 | Hayashi et al. |
| 6,384,949 B1 | 5/2002 | Suzuki |
| 6,456,314 B1 | 9/2002 | Masuda |
| 6,462,879 B2 | 10/2002 | Masuda |
| 6,496,214 B1 | 12/2002 | Masuda et al. |
| 6,686,946 B2 | 2/2004 | Masuda et al. |
| 6,717,606 B2 | 4/2004 | Masuda |
| 6,724,414 B2 | 4/2004 | Masuda et al. |

(Continued)

FOREIGN PATENT DOCUMENTS

| | | |
|---|---|---|
| EP | 1 457 840 | 9/2004 |
| JP | 64-35466 | 2/1989 |

(Continued)

*Primary Examiner* — Walter L Lindsay, Jr.
*Assistant Examiner* — Frederick Wenderoth
(74) *Attorney, Agent, or Firm* — Dickstein Shapiro LLP

(57) ABSTRACT

A toner density is calculated from outputs of light-receiving elements based on a difference between a reflection property of a supporting member and a reflection property of a toner pattern. Light-emitting elements aligned in one direction that is inclined to a sub-direction emit a detection light in such a manner that a distance between adjacent spots falling on the supporting member in a second direction is equal to or smaller than a width of the toner pattern in the second direction. The light-receiving elements receive a reflected light reflected from the supporting member and/or the toner pattern. The light-receiving elements are aligned, opposed to the supporting member, in a one direction corresponding to the light-emitting elements.

13 Claims, 11 Drawing Sheets

(56) References Cited

U.S. PATENT DOCUMENTS

| | | |
|---|---|---|
| 6,959,157 B2 | 10/2005 | Nakayama |
| 6,975,338 B2 | 12/2005 | Hirai et al. |
| 7,068,295 B2 | 6/2006 | Masuda |
| 7,193,642 B2 | 3/2007 | Hirai et al. |
| 7,804,513 B2 | 9/2010 | Masuda |
| 2004/0008245 A1 | 1/2004 | Hirai et al. |
| 2004/0208663 A1 | 10/2004 | Sakai et al. |
| 2005/0067944 A1 | 3/2005 | Masuda et al. |
| 2005/0093963 A1 | 5/2005 | Masuda |
| 2006/0256183 A1 | 11/2006 | Masuda |
| 2007/0146473 A1 | 6/2007 | Masuda |
| 2008/0075492 A1 | 3/2008 | Mestha et al. |
| 2008/0084594 A1 | 4/2008 | Masuda |

FOREIGN PATENT DOCUMENTS

| | | |
|---|---|---|
| JP | 2002-72612 | 3/2002 |
| JP | 2003-84530 | 3/2003 |
| JP | 2004-21164 | 1/2004 |
| JP | 2004-53944 A | 2/2004 |
| JP | 2005-271574 A | 10/2005 |
| JP | 2007-30254 | 2/2007 |
| JP | 2007-298854 | 11/2007 |
| JP | 2008-40454 | 2/2008 |
| JP | 4154272 | 7/2008 |

MAIN DIRECTION

SUB-DIRECTION

TONER-DENSITY CALCULATING METHOD, REFLECTIVE OPTICAL SENSOR, REFLECTIVE OPTICAL SENSOR DEVICE, AND IMAGE FORMING APPARATUS

CROSS-REFERENCE TO RELATED APPLICATIONS

This application is a divisional of U.S. application Ser. No. 13/539,511, filed on Jul. 2, 2012, which is now continuation of U.S. application Ser. No. 12/399,356, filed on Mar. 6, 2009, now U.S. Pat. No. 8,260,164, the entire disclosure of which is incorporated herein by reference thereto, and incorporates by reference the entire contents of Japanese priority document 2008-070198, filed in Japan on Mar. 18, 2008, and Japanese priority document 2008-238451, filed in Japan on Sep. 17, 2008.

BACKGROUND OF THE INVENTION

1. Field of the Invention

The present invention relates to a technology for calculating a toner density.

2. Description of the Related Art

A variety of image forming apparatuses use toner to form images, i.e., they form toner images. Example of such image forming apparatuses are analog image forming apparatuses, digital image forming apparatuses, black-and-white copiers, color copiers, printers, plotters, facsimile machines, and, multifunction printers (MFPs).

To form a good quality toner image, as is widely known, an electrostatic latent image needs to be developed with just an appropriate amount of toner. The electrostatic latent image can be developed with a two-component developer that contains toner and carrier or a single-component developer that contains only toner. An amount of the toner to be supplied to a developing unit that develops the electrostatic latent image is called, hereinafter, "toner density".

If the toner density is low, i.e., if the amount of the toner supplied to the electrostatic latent image is less than the necessary amount, a paler toner image will be formed. If the toner density is high, i.e., if the amount of the toner supplied to the electrostatic latent image is more than the necessary amount, a darker and difficult-to-see toner image will be formed. To form a good quality toner image, the toner density should be within an appropriate range.

To adjust the toner density to a value within the appropriate range, it is necessary to measure the current toner density. In a typical method, the toner density is measured from a change in a detection light reflected from a toner image that is formed dedicated to the toner-density measurement (hereinafter, "toner pattern"). An optical device that emits the detection light to the toner pattern and receives the detection light reflected from the toner pattern is called a reflective optical sensor.

Various types of reflective optical sensors are known in the art (see Japanese Patent Application Laid-open No. S64-35466, Japanese Patent Application Laid-open No. 2004-309292, Japanese Patent Application Laid-open No. 2004-21164, and Japanese Patent Application Laid-open No. 2002-72612).

Typical reflective optical sensors include a light-emitting unit and a light-receiving unit. The light emitting unit includes one, two, or three light-emitting elements having different wavelength characteristics. The light-receiving unit includes one or two light-receiving elements (e.g., photo-diodes (PDs) or phototransistors).

Light-emitting diodes (LEDs)) are typically used as the light-emitting elements. The LEDs emits the detection light of a spot size that is smaller than the toner pattern on the toner pattern.

The toner pattern is formed, for example, on a transfer belt. The toner pattern moves as the transfer belt rotates. A direction in which the transfer belt moves due to the rotation is called a sub-direction, and a direction perpendicular to the sub-direction is called a main-direction. In a system in which electrostatic latent images are formed through optical scanning, the main-direction corresponds to the main-scanning direction, and the sub-direction corresponds to the sub-scanning direction.

An electrostatic latent image corresponding to a toner pattern is formed on a photosensitive member by optically scanning a surface of the photosensitive member with an electrostatic-latent-image forming unit, and the electrostatic latent image on the surface of the photosensitive member is then developed into the toner pattern. The toner pattern on the photosensitive member is then transferred onto the transfer belt, and is moved in the sub-direction with the rotation of the transfer belt. When the toner pattern enters a detection area, the toner pattern is exposed with a spot of the detection light from the reflective optical sensor. The spot size of the spot of the detection light is typically about 2 millimeters (mm) to 3 mm.

In an ideal situation, the spot falls on the center of the toner pattern in the main-direction. However, it is difficult to always keep a relative position between the toner pattern and the reflective optical sensor in the main-direction the ideal state, due to various reasons. These reasons include fluctuation in an optical scanning area of the electrostatic-latent-image forming unit, meandering of the transfer belt, positional shift of the reflective optical sensor in the main-direction from an initial installation position because of passage of time.

If a portion of the spot falls in a region where there is no toner pattern because of the positional miss-match in the main-direction between the toner pattern and the reflective optical sensor, the reflected light received by the light-receiving unit represents wrong data, and therefore the measured toner density is wrong. Assume, for example, that one light-emitting element emits one spot of the detection light, one light-receiving element receives the reflected light, and the toner density is calculated from a difference between a specular reflection light and a diffuse reflection light. The light-receiving element is arranged to receive the specular reflection light. If a first portion of the spot falls in a region where there is no toner pattern and a second portion falls on the toner pattern, the first portion of the detection light is reflected specularly while the second portion is reflected diffusely. As a result, in a configuration where the light-receiving element is arranged so as to receive the specular reflection light, as compared to a case where the entire spot falls out of the toner pattern, intensity of the specular reflection light that is received at the light-receiving element decreases due to the generation of the diffuse reflection light. The decrease in the intensity of the specular reflection light can also occur when the toner amount at the toner pattern is low. Therefore, the decrease in the intensity of the specular reflection light is due to low toner amount or miss-match between the spot and the toner pattern is always unclear.

To solve this problem, in the conventional techniques, the toner pattern of a size from about 15 mm to about 25 mm in both the main-direction and the sub-direction is formed so that the spot of the detection light cannot fall out of the toner pattern even in case of the positional miss-match.

In the image forming apparatuses, specifically, the color image forming apparatus, the measurement of the toner density by the reflective optical sensor using the toner pattern is performed to acquire and maintain high image quality as a maintenance activity necessary for an accurate image-forming process. Because the toner-density measurement is performed as the maintenance activity separated from the main activity, i.e., an image-forming process, the image formation cannot be performed during the toner-density measurement.

When the electrostatic latent image to be developed to the toner pattern is written by the optical scanning, time required for the optical scanning is in proportion to the size of the toner pattern. In other words, the larger the toner pattern is, the lower the operating efficiency of the image formation becomes.

Moreover, because a total amount of the toner in the toner container or the like is fixed, as an amount of the toner to be used for the toner pattern increases, an amount of the toner to be used for the main activity, i.e., the image formation decreases, disadvantageously. The larger the toner pattern is, the more the toner is consumed for the toner pattern. In this manner, the conventional toner-density measuring methods have the two disadvantages, i.e., the low operating efficiency and the large toner-consumption amount for the toner pattern.

SUMMARY OF THE INVENTION

It is an object of the present invention to at least partially solve the problems in the conventional technology.

According to an aspect of the present invention, there is provided a toner-density calculating method implemented on a toner image forming apparatus. The toner-density calculating method includes forming a predetermined toner pattern on a surface of a supporting member that moves in a first direction; emitting a detection light onto the supporting member with a light-emitting unit; receiving a reflected light reflected from at least one of the supporting member and the toner pattern with a light-receiving unit; and calculating a toner density of the toner pattern based on a difference between a reflection property of the supporting member to the detection light and a reflection property of the toner pattern to the detection light. The light-emitting unit includes M number of light-emitting elements aligned in a third direction that is inclined to the first direction, where M is equal to or larger than three, wherein the light-emitting elements emit the detection light so that M number of light spots fall on the supporting member in such a manner that a distance between adjacent light spots in a second direction that is perpendicular to the first direction in a plane of the supporting member is equal to or smaller than a width of the toner pattern in the second direction, the light-receiving unit includes N number of light-receiving elements that receive the reflected light from at least one of the supporting member and the toner pattern, where N is equal to or larger than three, wherein the light-receiving elements are aligned, opposed to the supporting member, in a single direction, corresponding to the light-emitting unit, and the calculating includes calculating the toner density from outputs of the light-receiving elements.

According to another aspect of the present invention, there is provided a reflective optical sensor for use in a toner image forming apparatus. The reflective optical sensor includes a light-emitting unit that emits a detection light onto a supporting member that moves in a first direction, the light-emitting unit including M number of light-emitting elements aligned in a fourth direction, where M is equal to or larger than three, the light-emitting elements turning ON/OFF individually or simultaneously; and a light-receiving unit that receives a reflected light reflected from at least one of the supporting member and a toner pattern formed on the supporting member, the light-receiving unit including N number of light-receiving elements aligned in a fifth direction corresponding to the light-emitting unit, where N is equal to or larger than three.

According to still another aspect of the present invention, there is provided a toner-density calculating method implemented on a toner image forming apparatus. The toner-density calculating method includes forming a predetermined toner pattern on a surface of a supporting member that moves in a first direction; emitting a detection light onto the supporting member with a light-emitting unit; receiving a reflected light reflected from at least one of the supporting member and the toner pattern with a light-receiving unit; and calculating a toner density of the toner pattern based on a difference between a reflection property of the supporting member to the detection light and a reflection property of the toner pattern to the detection light. The light-emitting unit includes M number of light-emitting elements aligned in a third direction that is inclined to the first direction, where M is equal to or larger than three, the light-emitting elements emit the detection light so that M number of light spots fall on the supporting member in such a manner that a distance between adjacent light spots in a second direction that is perpendicular to the first direction in a plane of the supporting member is equal to or smaller than a width of the toner pattern in the second direction, the light-receiving unit includes N number of light-receiving elements that receive the reflected light reflected from at least one of the supporting member and the toner pattern, where N is equal to or larger than three, the light-receiving elements are aligned, opposed to the supporting member, in a single direction, corresponding to the light-emitting unit, the emitting includes emitting the detection light sequentially from the M light-emitting elements. The calculating includes when a first light-emitting element emits the detection light, categorizing an output of a first light-receiving element corresponding to the first light-emitting element to a specular reflection output representing specular reflection light, and categorizing outputs of non-corresponding light-receiving elements to the first light-emitting element to diffuse reflection outputs representing diffuse reflection light; and calculating the toner density based on categorized outputs of the light-receiving elements.

The above and other objects, features, advantages and technical and industrial significance of this invention will be better understood by reading the following detailed description of presently preferred embodiments of the invention, when considered in connection with the accompanying drawings.

DETAILED DESCRIPTION OF THE PREFERRED EMBODIMENTS

Figure 1:
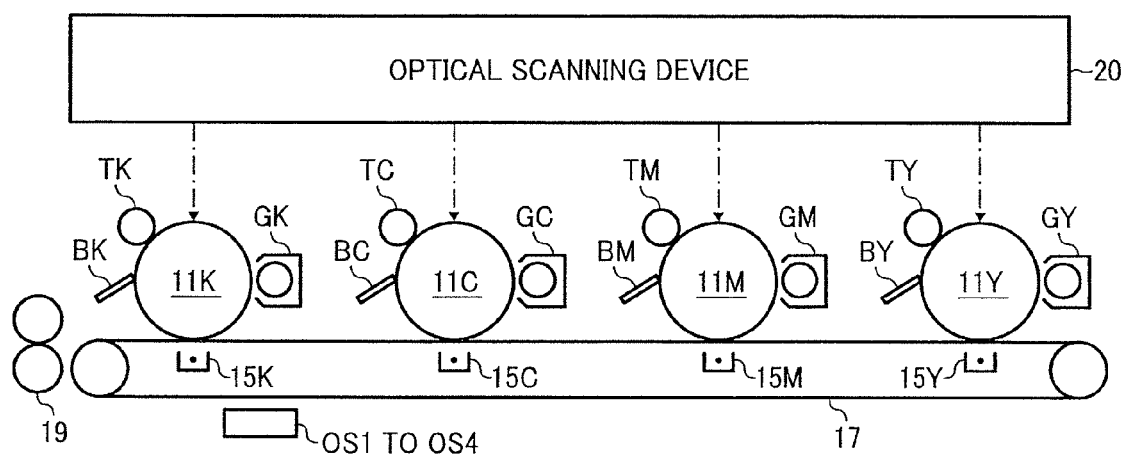
FIG. 1 is a schematic diagram of an image forming apparatus according to a first embodiment of the present invention.

Exemplary embodiments of the present invention are described in detail below with reference to the accompanying drawings.

The method of forming images with toner is used in the copiers, the printers, the plotters, the facsimile machines, the MFPs, etc. The method of forming images with toner includes the process of forming the electrostatic latent image and the process of developing the electrostatic latent image to the toner image. The process of forming the electrostatic latent image is, more particularly, the process of exposing a photoconductive latent-image carrier with an evenly-charged surface to a light by the optical scanner or the like.

The toner pattern is a toner image for the toner-density measurement. The toner pattern is formed by developing a predetermined electrostatic latent image. The toner pattern is on a supporting member in the measurement. In other words, the toner pattern is formed on the supporting member and then is moved in the sub-direction to the detection area.

The electrostatic latent image to be developed to the toner pattern can be formed by exposure of an image with a pattern having a predetermined density or by writing by the optical scanning.

As described above, the supporting member moves, in the toner-density measurement, in the sub-direction, carrying the toner pattern thereon. The supporting member can be, for example, a latent-image carrier on which the electrostatic latent image is formed and a transfer belt or an intermediate transfer belt that is used to transfer the toner image.

In the following description, "predetermined toner pattern" means that a shape of the toner pattern is fixed. Moreover, "single direction intersecting the sub-direction" includes the direction perpendicular to the sub-direction, i.e., the main-direction. "Distance between adjacent spots in a direction perpendicular to the sub-direction" means a distance between adjacent ones of spots formed on the surface of the supporting member aligned in the single direction perpendicular to the sub-direction, i.e., the main-direction when each of M−number of the light-emitting elements emits the detection light. Moreover, "distance between adjacent spots" means not a distance between centers of the adjacent spots in the main-direction but, if the adjacent spots are not overlapped with each other, a distance between circumferences of the adjacent spots in the main-direction.

Specifically, it is assumed in the following description that M−number of the light-emitting elements are aligned in the main-direction at a 3-mm pitch, and the diameter of the circular spots is 2 mm. In other words, the distance between adjacent spots is 1 mm in the main-direction. This 1-mm interval between the adjacent spots is not exposed to the detection light.

However, if the toner pattern is larger than the distance between the adjacent spots (1 mm) in the main-direction, at least a part of the toner pattern is exposed to any of the spots when the toner pattern passes through an area on which the spots are aligned. Therefore, it is enough for the toner pattern to be a little larger than 1 mm in the main-direction to be exposed to the spots of the detection light. In other words, a toner pattern that is much smaller than the conventional toner pattern (15 mm to 25 mm) in width in the main-direction is sufficient.

The distance between the adjacent spots in the direction perpendicular to the sub-direction should be set smaller than the width of the toner pattern in the main-direction. That is, the distance between the adjacent spots can be smaller than 1 mm, and, moreover, the adjacent spots can have an overlap in the main-direction. If the adjacent spots are overlapped, the distance between adjacent spots is a minus value, and the areas that are exposed to the spots of the detection light make a single area continuous in the main-direction. Therefore, the width of the toner pattern in the main-direction can be decreased infinitely, in principal.

Moreover, even if the spot size is smaller than the width of the toner pattern in the main-direction, it is possible to expose without fail the toner pattern to the detection light by adjusting the pitch between the adjacent spots in the main-direction to a value smaller than the width of the toner pattern in the main-direction. This is because, by the adjustment, the distance between the adjacent spots in the main-direction becomes smaller than the width of the toner pattern in the main-direction.

When the light-emitting unit emits the detection light to the supporting member, the detection light is reflected from the surface of the supporting member and/or the toner pattern, and is received by the light-receiving unit. The light-receiving unit includes three or more light-receiving elements. The intensity of the light received at each of the light-receiving elements varies depending on a positional relation between the spots of the detection lights and the toner pattern. The toner density is measured accurately from outputs of the three or more light-receiving elements.

As is widely known, when the detection light strikes the toner pattern, the detection light is diffusely reflected. On the other hand, if the surface of the supporting member is specular and when the detection light strikes an area out of the toner pattern on a surface of the supporting member, the detection light is specularly reflected. The supporting member can be, for example, a photoconductive latent-image carrier.

Accordingly, the reflection property when the detection light strikes the area out of the toner pattern on the surface of the supporting member shows the specular reflection, while the reflection property when the detection light strikes the toner pattern shows the diffuse reflection. The difference in the reflection properties causes a variation of the intensities of the light received at the three or more light-receiving elements. Therefore, a degree of the toner darkness (i.e., the toner density) can be measured from outputs of the three or more light-receiving elements.

If a transfer belt or an intermediate transfer belt is used as the supporting member, the surface of the supporting member reflects, in some cases, the detection light substantially specularly almost as a mirror surface reflects, and reflects, in other cases, the detection light diffusely. Even in a case that the surface of the supporting member reflects the detection light diffusely, if there is a difference between the diffuse reflection from the area out of the toner pattern and the diffuse reflection from the toner pattern, a distribution of the intensities of the light received at the plural light-receiving elements when the detection light is diffusely reflected from the area out of the toner pattern differs from the distribution when the detection light is diffusely reflected from the toner pattern. Therefore, the toner density can be measured correctly.

In the following description, it is assumed that both M, which is the number of the light-emitting elements that form the light-emitting unit, and N, which is the number of the light-receiving elements that form the light-emitting unit, are equal to or larger than three. It is allowable to set M equal to N (M=N) or different from N (M≠N). Moreover, it is allowable to set M larger than N (M>N) or M smaller than N (N<M).

Three or more LEDs aligned in a single direction can be used as the light-emitting elements of the light-emitting unit. If the LEDs have a lens function of collecting divergent light, the LEDs are arranged in such a manner that the detection light forms the sport with a desired size on the supporting member.

Alternatively, an LED array including three or more light-emitting elements can be used as the light-emitting unit. In this case, a light-collection optical system can be included in the light-emitting unit to collect the light emitted from the LED array.

PDs can be used as the light-receiving elements of the light-receiving unit. Alternatively, a PD array including three or more PDs (e.g., charge-coupled device (CCD) line sensor) can be used as the light-receiving unit.

The lower limit of M or N is, as described above, three. The upper limit of M or N is determined appropriately based on the practical size of the reflective optical sensor for the toner-density measurement. The upper limit of M is, preferably, about 500. The upper limit of N can be several thousands as large as the number of PDs in the above-described PD array.

The light-emitting elements in total of M can be tuned ON/OFF in various manners. For example, all the light-emitting elements turn ON/OFF, simultaneously. Alternatively, the light-emitting elements turn ON/OFF, sequentially one after another. Still alternatively, the light-emitting elements are categorized into several groups. For example, even-number groups and odd-number groups are arranged alternately. The light-emitting elements turn ON/OFF sequentially on the group basis from a group arranged on an end.

M is equal to P·m. The light-emitting unit includes P−number of groups each including m−number of light-emitting elements. A first light-emitting element of each group turns ON/OFF, i.e., the first light-emitting elements in total of P turn ON/OFF, simultaneously. After that, a second light-emitting element of each group turns ON/OFF, i.e., the second light-emitting elements in total of P turn ON/OFF, simultaneously. This ON/OFF operation is repeated until m-th light-emitting element of each group turns ON/OFF.

The toner pattern is a toner image having a fixed shape that is formed to measure the toner density. The toner pattern can be, for example, a homogenous toner image representing a reference density. The image forming apparatus determines whether the toner density is higher than the reference density based on degree of the darkness of the toner image. Alternatively, as described later, the toner pattern can be a collection of toner images each representing different reference densities. Although each of the toner images is the toner pattern, the collection of the toner images can be called "toner pattern". Still alternatively, the different toner images form a single pattern. In other words, this single pattern is a gradation image having various toner densities gradually changed.

The light-emitting unit includes M−number of the light-emitting elements, where M≥3, aligned in a single direction. The light-emitting elements turn ON/OFF individually or simultaneously.

The light-receiving unit includes N−number of the light-receiving elements, where N≥3, aligned in a single direction corresponding to the light-emitting unit.

The light-emitting unit can include M−number of individual LEDs as the light-emitting elements. Alternatively, the light-emitting unit can be, for example, an LED array including M−number of LEDs. The light-receiving unit can include N−number of individual PDs as the light-receiving elements. Alternatively, the light-receiving unit can be, for example, a PD array including N−number of PDs.

In the following description "the light-emitting elements and the light-receiving elements are aligned in a single direction" includes not only the light-emitting elements and the light-receiving elements aligned in one line extending in the single direction but also the light-emitting elements and the light-receiving elements aligned in several parallel lines extending in the single direction. The several lines on which the light-emitting elements and the light-receiving elements are aligned are, of course, parallel to or intersecting the main-direction. The several lines are parallel to each other.

Image forming apparatuses can perform a toner-density measurement method according to any of embodiments of the present invention by using the reflective optical sensor.

If the number of the light-receiving elements non-corresponding to a certain one of the light-emitting elements is N−3 or N−2, the number of the light-emitting elements (M) is equal to the number of the light-receiving elements (N), i.e., the light-emitting elements are corresponding to the light-receiving elements in a one-to-one manner. When the certain light-emitting element is arranged other than both ends, the number of the non-corresponding light-receiving elements is N−3. When the certain light-emitting element is arranged on an end, the number of the non-corresponding light-receiving elements is N−2. In another case, the number of the non-corresponding light-receiving elements is N−(2n+1), when the certain light-emitting element is arranged other than both ends; and is N−2n when the certain light-emitting element is arranged on an end, where n is a natural number.

An image forming apparatus according to a first embodiment of the present invention is described with reference to FIG. 1.

The image forming apparatus illustrated in FIG. 1 is a color image forming apparatus; however, the following description will apply even to a monochrome image forming apparatus. A color image is formed with four toners including yellow (Y), magenta (M), cyan (C), and black (K).

The image forming apparatus includes an optical scanning device 20. The optical scanning device 20 can be any widely-known scanner.

The image forming apparatus includes drum-shaped photosensitive elements 11Y, 11M, 11C, and 11K as photoconductive latent-image carriers. The photosensitive element 11Y is used for forming a yellow toner image, the photosensitive element 11M is for a magenta toner image, the photosensitive element 11C is for a cyan toner image, and the photosensitive element 11K is for a black toner image.

The optical scanning device 20 writes images onto the photosensitive elements 11Y, 11M, 11C, and 11K by the optical scanning. The photosensitive elements 11Y, 11M, 11C, and 11K are rotated in a clockwise direction at a constant speed, charged evenly by charging rollers TY, TM, TC, and TK as charging units, and scanned by the optical scanning device 20. Thus, electrostatic latent images (negative latent images) for yellow, magenta, cyan, and black are written onto the photosensitive elements 11Y, 11M, 11C, and 11K, respectively.

Those electrostatic latent images are developed by developing devices GY, GM, GC, and GK, and thus the yellow toner image, the magenta toner image, the cyan toner image, and the black toner image are formed on the photosensitive elements 11Y, 11M, 11C, and 11K, respectively as positive images.

The toner images are transferred onto a recording sheet (not shown) (e.g., transfer paper and plastic sheet for overhead projector) via a transfer belt 17.

The recording sheet is conveyed from a sheet table (not shown) that is arranged under the transfer belt 17 to an upper-right circumference of the transfer belt 17 illustrated in FIG. 1. After that, the recording sheet is attached to the transfer belt 17 by the exertion of the electrostatic force, and is conveyed to the left side of FIG. 1 by counterclockwise rotation of the transfer belt 17. The recording sheet sequentially receives, while being conveyed, the yellow toner image from the photosensitive element 11Y by a transfer member 15Y, the magenta toner image from the photosensitive element 11M by a transfer member 15M, the cyan toner image from the photosensitive element 11C by a transfer member 15C, and the black toner image from the photosensitive element 11K by a transfer member 15K.

In this manner, a full-color image is formed on the recording sheet in a superimposed manner. After that, the full-color image is fixed onto the recording sheet by a fixing device 19. The recording sheet with the full-color image is discharged out of the image forming apparatus. The full-color image can be formed onto an intermediate transfer belt in the superimposed manner and then transferred from the intermediate transfer belt to the recording sheet, instead of directly being formed on the recording sheet.

The image forming apparatus illustrated in FIG. 1 includes reflective optical sensors OS1 to OS4. In the image forming apparatus, the images are written onto the photosensitive elements 11Y, 11M, 11C, and 11K by the optical scanning as described above. The main-scanning direction in the optical scanning is a direction perpendicular to the drawing of FIG. 1 called "main-direction". A method of measuring the toner density by using the reflective optical sensors OS1 to OS4 is described below.

The optical scanning device 20 writes a certain electrostatic latent image onto each of the photosensitive elements 11Y, 11M, 11C, and 11K; the developing devices GY, GM, GC, and GK develop the electrostatic latent images to the toner images; the toner images are transferred from the photosensitive elements 11Y, 11M, 11C, and 11K directly to the surface of the transfer belt 17. Thus, the toner pattern is formed. It is clear from the above description that the transfer belt 17 works as "supporting member" in the first embodiment. This is why, the transfer belt 17 is called "supporting member 17", appropriately. The toner pattern is formed on the transfer belt 17, i.e., the supporting member, and is moved by the rotation of the transfer belt 17 to a detection area. After that, the toner-density measurement is performed by using the reflective optical sensors OS1 to OS4.

The toner pattern is removed from the surface of the transfer belt 17 by a cleaning device (not shown) arranged right, i.e., downstream of the reflective optical sensors OS1 to OS4.

Figure 2:
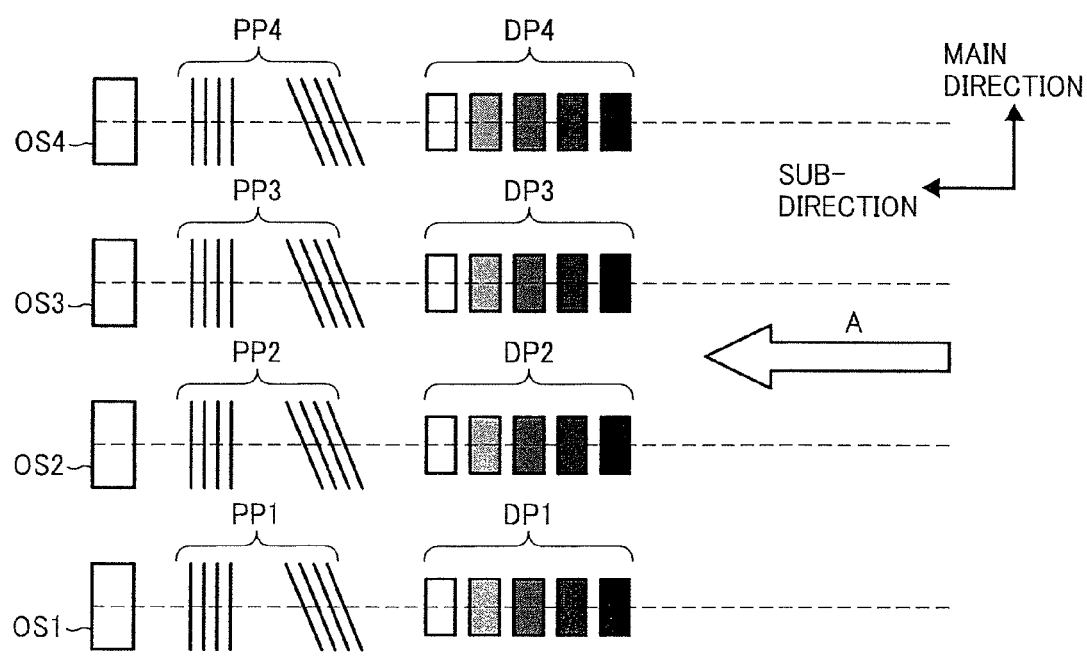
FIG. 2 is a schematic diagram for explaining toner-pattern detection performed by a reflective optical sensor illustrated in FIG. 1.

FIG. 2 is a schematic diagram for explaining a relation between the toner pattern that is formed on the transfer belt 17, i.e., the supporting member and the reflective optical sensors OS1 to OS4.

The direction in which the reflective optical sensors OS1 to OS4 are arranged in FIG. 2 is the main-direction. On the other hand, the direction, indicated by an arrow A, in which the transfer belt 17 rotates is the sub-direction.

Position detecting patterns PP1 to PP4 are used to detect positions of the toner images in yellow to black, respectively. Toner patterns DP1 to DP4 are used to measure the toner density.

The toner pattern DP1 is used for the measurement of the yellow toner density, the toner pattern DP2 is for the magenta toner density, the toner pattern DP3 is for the cyan toner density, and the toner pattern DP4 is for the black toner density.

In other words, the reflective optical sensors OS1 to OS4 detect positions of the toner images at four points aligned in the main-scanning direction. Moreover, the reflective optical sensor OS1 measures the yellow toner density, the reflective optical sensor OS2 measures the magenta toner density, the reflective optical sensor OS3 measures the cyan toner density, and the reflective optical sensor OS4 measures the black toner density.

In the example illustrated in FIG. 2 the toner patterns DP1 to DP4 are aligned in the main-direction; however, it is possible to align the toner patterns DP1 to DP4 in the sub-direction. In the later case, the reflective optical sensor OS1 sequentially measures the various toner densities. It is allowable to stop operation of the reflective optical sensor OS4 and detect the position detecting patterns PP1 to PP3 at the three points aligned in the main-scanning direction by using the other three reflective optical sensors OS1 to OS3.

As illustrated in FIG. 2, the position detecting patterns PP1 to PP4 are formed on certain positions of the transfer belt 17 to be opposed to the reflective optical sensors OS1 to OS4, respectively. Each of the position detecting patterns PP1 to PP4 includes four pairs of line patterns. Each pair includes a parallel line parallel to the main-direction and a slant line incline not parallel to the main-direction. The four pairs are formed with the yellow toner, the magenta toner, the cyan toner, and the black toner.

Although the reflective optical sensor detects the toner pattern that is formed on the transfer belt 17 that is used to convey the recording sheet and transfer the toner image onto the recording sheet in the first embodiment, the reflective optical sensor can be configured to detect the toner pattern that is formed on the photosensitive element as the latent-image carrier or the intermediate transfer belt (or intermediate transfer medium).

Figure 3A:
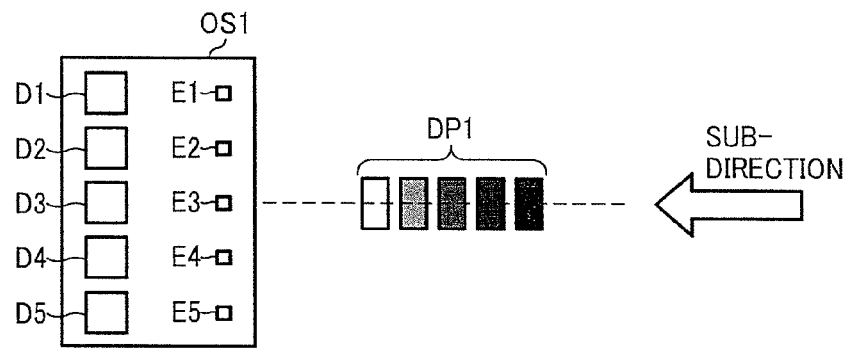
FIGS. 3A to 3F are schematic diagrams for explaining the toner-pattern detection by the reflective optical sensor.

The reflective optical sensors OS1 to OS4 and the measurement of the toner pattern are described below. The four reflective optical sensors OS1 to OS4 have the same structure, and therefore only the reflective optical sensor OS1 is described. FIG. 3A is a schematic diagram of the reflective optical sensor OS1. The arrow in FIG. 3A corresponds to the sub-direction and a direction perpendicular to the sub-direction in the plane of the paper corresponds to the main-direction.

The reflective optical sensor OS1 includes a light-emitting unit and a light-receiving unit. The light-emitting unit and the light-receiving unit are accommodated in housing as a unit. The light-emitting unit includes M−number of light-emitting elements E1 to E5 (M=5) that emits a detection light. The light-emitting elements E1 to E5 are aligned parallel to the main-direction at an equal pitch. The light-receiving unit includes N−number of light-receiving elements D1 to D5 (N=5) that receives a reflected light. The light-receiving elements D1 to D5 are also aligned parallel to the main-scanning direction at an equal pitch, corresponding to the light-emitting elements E1 to E5. The reflective optical sensor OS1 is arranged at the lower position on the transfer belt 17 as illustrated in FIG. 1.

Figure 3B:
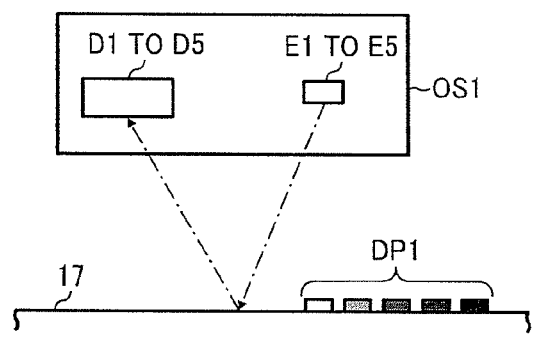

The light-emitting elements E1 to E5 are aligned in the main-direction on positions corresponding to the light-receiving elements D1 to D5, respectively. As illustrated in FIG. 3B, when the light-emitting element Ei, where i is an arbitrary integer from 1 to 5, emits the detection light to the surface of the transfer belt 17 as the supporting member, the corresponding light-receiving element Di receives the detection light reflected from the transfer belt 17. It means that the pitch between adjacent ones of the light-receiving elements D1 to D5 is equal to the pitch between adjacent ones of the light-emitting elements E1 to E5.

To make the description simpler, the surface of the transfer belt 17 is assumed to be specular. When the light-emitting element emits the detection light, the corresponding light-receiving element receives the detection light specularly reflected from the surface of the transfer belt 17.

That is, the reflected light, illustrated in FIG. 3B that any of the light-receiving elements D1 to D5 receives is a specular light reflected from the surface of the transfer belt 17.

The light-emitting elements E1 to E5 are, for example, LEDs. The light-receiving elements D1 to D5 are, for example, PDs.

The pitch of the light-emitting elements E1 to E5 is set to such a value that, when the light-emitting elements E1 to E5 emit the detection light and five spots of the detection light are formed on the surface of the transfer belt 17 aligned in the main-scanning direction, a distance between adjacent ones of the spots is smaller than a width of the toner pattern DP1 in the main-direction.

As described above, the toner pattern DP1 illustrated in FIG. 3A is formed with the yellow toner. The toner pattern DP1 includes various rectangular toner patterns (five patterns in FIG. 2) having different gradated densities. In other words, the toner pattern DP1 is a collection of the five rectangular having different toner densities. Those rectangular toner patterns having different toner densities are formed by adjusting a laser power in the optical scanning, a duty in the emission light, or a developing bias.

As illustrated in FIGS. 3A and 3B, the toner pattern DP1 is formed on the surface of the transfer belt 17 as the supporting member, and then is moved toward the detection area of the reflective optical sensor OS1.

Timing when the toner pattern DP1 is formed and time required for the toner pattern DP1 to move to the detection area are substantially fixed. When the toner pattern DP1 approaches the detection area, the light-emitting elements E1 to E5 start ON/OFF.

The detection of the position detecting pattern PP1 is performed before the detection of the toner pattern DP1. The detection of the position detecting pattern PP1 will be described later.

The size of the spot, which are formed on the surface of the transfer belt 17 when the light-emitting elements E1 to E5 emit the detection light, is set to, for example, 2 mm smaller than the pitch of the light-emitting elements E1 to E5 of, for example, 3 mm. The five spots are aligned in the main-direction on the transfer belt 17.

The width of each of the rectangular toner patterns of the toner pattern DP1 in the main-direction is set to, for example, 2.5 mm smaller than the pitch of the light-emitting elements E1 to E5 of, for example, 3 mm.

That is, the distance between the adjacent spots in the main-direction is 1 mm, which is smaller than the width of the rectangular toner pattern in the main-direction of 2.5 mm.

The light-emitting elements E1 to E5 turn ON/OFF, sequentially starting from the light-emitting element E1 to the light-emitting element E5. More particularly, the light-emitting element E1 turns ON and then OFF, firstly. The light-emitting element E2 turns ON and then OFF, secondly. After that, the light-emitting element E3 turns ON and then OFF, thirdly. Subsequently, the light-emitting element E4 and then the light-emitting element E5 turn ON/OFF, in the same manner.

The ON/OFF operation of those light-emitting elements E1 to E5 is repeated at a high speed. Thus, the surface of the transfer belt 17 is scanned in the main-direction over and over with the five spots of the detection light. This operation is called, hereinafter, "spot scanning with the detection light".

As described above, the surface of the transfer belt 17 is specular. If the detection light strikes an area out of the toner pattern, the reflected detection light is the specular light. The light-receiving element Di, where i is an arbitrary integer from 1 to 5, is in position to receive, when the detection light is specularly reflected from the area out of the toner pattern, the specular light that has been emitted from the corresponding light-emitting element Ei only.

Figure 3C:
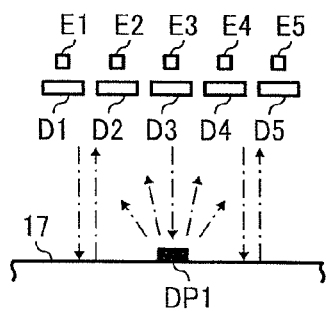

Consider, for example, a case where the center of the toner pattern DP1 in the main-direction falls on the spot of the detection light that is emitted from the light-emitting element E3 under the above-described conditions. As illustrated in FIG. 3C, when the light-emitting elements E1, E2, E4, and E5 emit the detection light to the transfer belt 17, the detection light is specularly reflected from the surface of the transfer belt 17, and then is received at the light-receiving elements D1, D2, D4, and D5, respectively.

On the other hand, when the light-emitting element E3 turns ON and emits the detection light to the toner pattern DP1, a part of the detection light is specularly reflected and the other part of the detection light is diffusely reflected the toner pattern DP1.

An amount of the specular reflection component received at the light-receiving element D3 decreases by an amount of the diffusion reflection component. The diffusion reflection light is received at the other light-receiving elements D1, D2, D4, and D5.

As a result, in the case where the light-emitting element E3 emits the detection light, an output of the light-receiving element D3 is relatively low (lower than the value when the detection light falls in a region where there is no toner pattern), while outputs of the other light-receiving elements D1, D2, D4, and D5 are larger than zero.

It is possible to recognize from a result of the outputs that the toner pattern DP1 (one of the rectangular toner patterns of the toner pattern DP1) is on a position opposed to the light-emitting element E3 in the main-direction.

If the toner pattern is between the light-emitting elements E3 and E4, when the light-emitting element E3 turns ON, the output of the light-receiving element D3 is low, and when the light-emitting element E4 turns ON, the output of the light-receiving element D4 is low.

It is determined from a result of the outputs that the toner pattern is between the light-emitting elements E3 and E4 in the main-direction. If the output of the light-receiving element D3 is lower than the output of the light-receiving element D4, the toner pattern is closer to the light-emitting element E4.

In this manner, the position of the toner pattern DP1 in the main-direction can be detected accurately to one digit smaller than the pitch of the light-emitting elements E1 to E5 (e.g. down to about one-tenth of the pitch according to, for example, a ratio between the outputs of the light-receiving elements D3 and D4).

It means that, if, for example, 100 light-emitting elements E1 to EM (M=100) are aligned at a 100-μm pitch in the main-direction, the arrangement width is 10 mm.

A total of 100 light-receiving elements D1 to DN (N=100) are aligned in the main-direction at the 100-μm pitch in the same manner as the light-emitting elements E1 to EM. When the light-emitting element Ei, where i is an arbitrary integer from 1 to 100, emits the detection light to the supporting member, the detection light is specularly reflected, and is received at the corresponding light-receiving element Di. The width of the toner pattern in the main-direction is equal to the pitch of the light-emitting elements E1 to EM of 100 μm. A change in the output of the light-receiving element Di is analyzed, while the light-emitting elements E1 to E100 turn ON/OFF sequentially. If, when a light-emitting element Ej and a light-emitting element Ej+1 turn ON, the output of a light-receiving element Dj and the output of a light-receiving element Dj+1 are low, it is determined the that toner pattern is between the light-emitting elements Ej and Ej+1 in the main-direction.

In other words, the position of the toner pattern having 100 μm in width in the main-direction can be detected accurately by one digit smaller than 100 μm.

It is easy to implement the arrangement of 100 light-emitting elements at the 100-μm pitch, if an LED array is used. Moreover, it is easy to implement the arrangement of 100 light-receiving elements at the 100-μm pitch, if a PD array is used. Even several tens- to several hundreds-μm pitch LED and PD arrays are available.

A reflective optical sensor including LEDs individually working as the light-emitting elements E1 to E5 and PDs individually working as the light-receiving elements D1 to D5 can be used as the reflective optical sensor OS1 according to the first embodiment. The LEDs and the PDs are formed by resin molding or by surface mounting at an integrated and high-density manner. If extremely small LEDs and PDs dimensions of which can be adjusted in the millimeter are used, the pitch can be decreased to about 1 mm.

By using extremely small LEDs and PDs the position of the toner pattern with 1 mm in the width in the main-direction can be detected accurately down to the millimeter.

As described above, the toner pattern DP1 is used to measure the yellow toner density. The toner pattern DP1 includes the five rectangular toner patterns having different gradated densities aligned in the sub-direction at the predetermined pitch.

If, for example, the spot of the detection light emitted from the light-emitting element E3 falls on the toner pattern while the light-emitting elements E1 to E5 turn ON/OFF sequentially, the intensity of the specular reflection light received at the light-receiving element D3 decrease while the outputs of the other light-receiving elements increase by the amount of the diffuse reflection light.

The amount of the specular reflection light is inversely proportional to the toner density, while the amount of the diffusion reflection light is directly proportional to the toner density.

Therefore, the toner density of the toner pattern can be measured from the output of the light-receiving element D3 representing the specular reflection light and the outputs of the other light-receiving elements. More particularly, those outputs are amplified by an amplifier (not shown), and then subjected to a desired signal processing. After that, the toner density is calculated from the processed signal by using a toner-density calculating process.

An algorism for calculating the toner density is determined experimentally based on a practical embodiment of the image forming apparatus.

In this manner, the toner density is measured accurately by emitting the detection light from the reflective optical sensor to the correct position of the toner pattern.

Moreover, because the light-emitting elements and the light-receiving elements that are aligned at a very small pitch, even if the width of the toner pattern in the main-direction is small, the position of the toner pattern in the main-direction is detected accurately in such small unit the same as the pitch.

In the first embodiment, if independent extremely small LEDs and PDs aligned at about 1-mm pitch are used as the light-emitting elements E1 to E5 and the light-receiving elements D1 to D5, the width of the toner pattern DP1 in the main-direction is enough to about 1 mm. If the toner pattern DP1 includes the five rectangular toner patterns as illustrated in FIG. 3A, the width of each toner pattern in the sub-direction is enough to smaller than about 1 mm.

Then, the area of the toner pattern DP1 is 5 mm$^2$, which is equal to 1/125 of the conventional toner pattern of 25 mm×25 mm. Because the area of the toner pattern DP1 is small, the toner pattern DP1 can be formed within a short time. This makes it possible to suppress a reduction in the operating efficiency of the image formation. Moreover, the amount of the toner for the toner pattern is remarkably decreased to 1/125 in the same ratio as the area of the toner pattern is decreased.

The reflective optical sensor can detect the relative position of the toner images in the sub-direction and the positions of the toner images in the main-direction by using the position detecting pattern PP1 or the like.

Figure 3D:
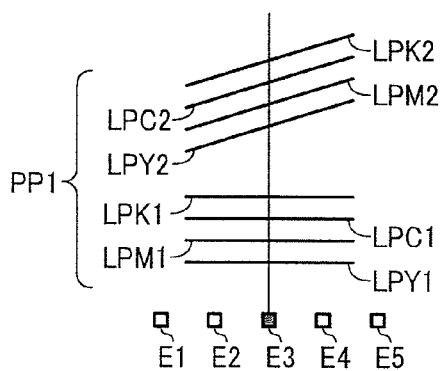
Figure 3E:
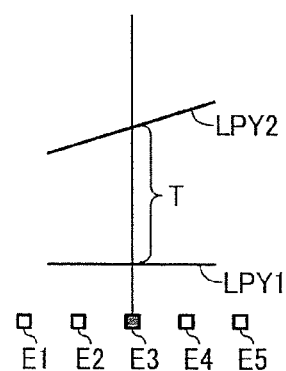
Figure 3F:
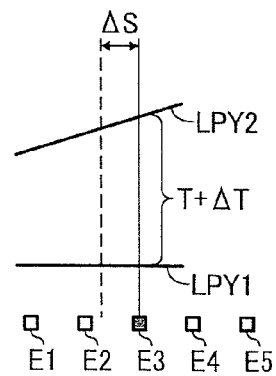

FIGS. 3D to 3F are schematic diagrams for explaining the position detection by using the position detecting pattern PP1.

The position detecting pattern PP1 includes parallel line patterns LPY1, LPM1, LPC1, and LPK1 each parallel to the main-direction, and slant line patterns LPY2, LPM2, LPC2, and LPK2 each not parallel to the main-direction.

The line patterns LPY1 and LPY2 make a pair, and are formed with the yellow toner.

The line patterns LPM1 and LPM2 make a pair, and are formed with the magenta toner. The line patterns LPC1 and LPC2 make a pair, and are formed with the cyan toner. The line patterns LPK1 and LPK2 make a pair, and are formed with the black toner.

The four pairs of the line patterns are formed in such a manner that the pairs are to be aligned in the sub-direction at a fixed interval.

If the pairs are actually aligned at the fixed interval in the sub-direction, it is determined that the positional relation among the yellow toner image, the magenta toner image, the cyan toner image, and the black toner is correct in the sub-direction.

To determine whether the positional relation in the sub-direction is correct, for example as illustrated in FIG. 3D, the light-emitting element E3 turns ON when the position detecting pattern PP1 comes close to the detection area of the reflective optical sensor. The light-emitting element E3 is ON for a continuous time.

As the position detecting pattern PP1 moves, the spot of the detection light emitted from the light-emitting element E3 relatively moves in the sub-direction on the supporting member, thereby illuminating the line patterns LPY1 to LPK1 one by one.

When the detection light falls on any of the line patterns, the output of the light-receiving element D3, which receives the specular reflection light, decreases while the outputs of the other light-receiving elements, which receives the diffuse reflection light, increases. Therefore, time that the detection light takes to move through the intervals among the four line patterns can be measured by tracking the outputs of the light-receiving elements D1 to D5 in terms of time.

If the time intervals are equal, it is determined that the positional relation among the toner images in the sub-direction is correct. If the time intervals are not equal, it is determined that the positional relation is not correct. Moreover, a deviation amount in the positional relation can be measured from the change in the outputs. If the positional relation is not correct, the timing to start the optical scanning is adjusted based on the deviation amount.

On the other hand, the positional relation in the main-direction among the toner images is determined in the following manner. In the following description, the position of the yellow toner image is detected with reference to FIGS. 3E and 3F as an example.

FIG. 3E is a schematic diagram of the yellow toner image that is arranged in a correct position. It takes time T for the spot of the detection light to move from the line pattern LPY1 to the line pattern LPY2.

FIG. 3F is a schematic diagram of the yellow toner image that is arranged in an incorrect position deviated by $\Delta S$ in the main-direction. Because the line pattern LPY2 is not parallel to the line pattern LPY1, time required for the spot of the detection light to move from the line pattern LPY1 to the line pattern LPY2 is longer, i.e., T+$\Delta T$. Therefore, the deviation amount is calculated from $\Delta T$ that is a difference between T and T+$\Delta T$.

More particularly, the relation between $\Delta S$ and $\Delta T$ is as follows:

$$\Delta S \cdot \tan \theta = V \cdot \Delta T$$

where $\theta$ is angle between the line pattern LPY2 and the main-direction, and V is velocity of the transfer belt 17 as the supporting member in the sub-direction. Therefore, $\Delta S$ is calculated as follows:

$$\Delta S = V \cdot \Delta T \cdot \cot \theta$$

As described with reference to FIGS. 3A to 3C, in the reflective optical sensor OS1, the light-emitting elements E1 to E5 turn ON/OFF sequentially to detect the toner patterns. It takes a certain time from the ON/OFF of the light-emitting element E1 to the ON/OFF of the light-emitting element E5. The certain time is called "scanning time".

The toner pattern (i.e., individual rectangular toner patterns) should be within an area to be subjected to the spot scanning by the reflective optical sensor (i.e., area where the sequentially flashing spots of the detection light falls) (hereinafter, "scanning area") during the scanning time. In other words, the sequential ON/OFF of the light-emitting elements E1 to E5 are performed while the toner pattern is within the scanning area.

If M, which is the number of the light-emitting elements of the reflective optical sensor, is small, the scanning time will be short.

As described above, to maintain the operating efficiency of the image formation by decreasing the time to form the toner pattern and efficiently reduce the amount of the toner for the toner pattern, it is necessary that the toner pattern be small.

To correctly exposing the small toner pattern to the detection light, thereby measuring the correct toner density, it is necessary to decrease the pitch of the light-emitting elements and the light-receiving elements by an amount that corresponds to the decrease in the width of the toner pattern in the main-direction.

The length of the arrangement area of the light-emitting elements and the light-receiving elements is required to be about 10 mm in consideration for the miss-match between the toner pattern and the reflective optical sensor in the main-direction. As the pitch decreases, M, which is the number of the light-emitting elements, increases to a remarkably large number.

As M increases, the scanning time increases.

The supporting member with the toner pattern formed thereon moves by a distance V·st in the sub-direction for the scanning time, where st is scanning time and V is velocity of the supporting member moving in the sub-direction.

If M is too large while V is unchanged, the scanning time becomes longer than time required for the toner pattern to pass through the scanning area. If so, it is difficult to measure the correct toner density.

Figure 4A:
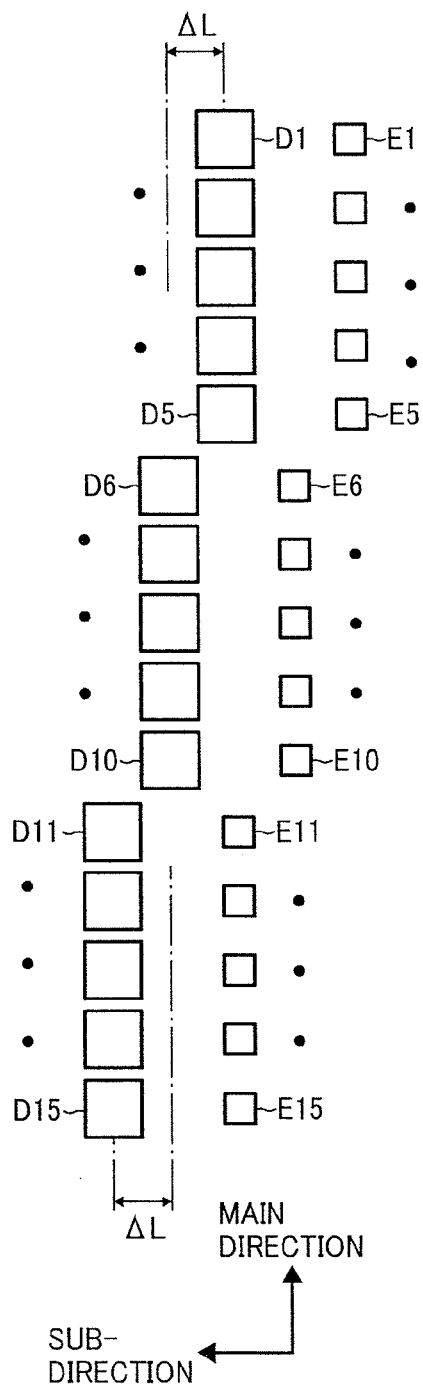
FIG. 4A is a schematic diagram of an arrangement of light-emitting elements and light-receiving in a reflective optical sensor according to a second embodiment of the present invention.
Figure 4B:
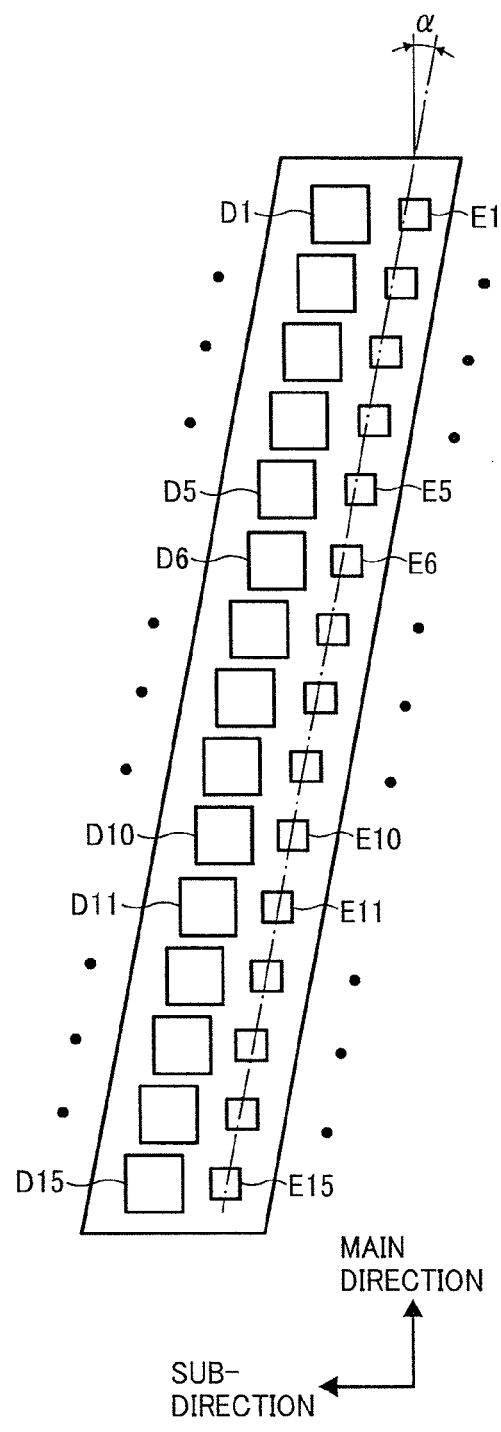
FIG. 4B is a schematic diagram of an arrangement of light-emitting elements and light-receiving in a reflective optical sensor according to a third embodiment of the present invention.

A second embodiment and a third embodiment of the present invention disclose a solution to this problem and those embodiments are described with reference to FIGS. 4A and 4B, respectively. Reflective optical sensors according to the second embodiment and the third embodiment include 15 light-emitting elements E1 to E15 and 15 light-receiving elements D1 to D15. The light-emitting elements E1 to E15 corresponds the light-receiving elements D1 to D15, respectively in the one-to-one manner. Although the light-emitting elements and the light-receiving elements illustrated in FIGS. 4A and 4B are 15, each, several tens to several hundreds of the light-emitting elements and the light-receiving elements are used in practice. To make the drawings simpler, the number of the light-emitting elements and the light-receiving elements is set to 15 in the second embodiment and the third embodiment. In other words, the light-emitting elements and the light-receiving elements can be more than 15 or less than 15.

In the second embodiment illustrated in FIG. 4A, the light-emitting elements E1 to E15 and the light-receiving elements D1 to D15 that are aligned in the main-direction sequentially with beginning with the light-emitting element E1 and the light-receiving element D1. Moreover, the light-emitting elements E1 to E15 and the light-receiving elements D1 to D15 that are divided into a first group, a second group, and a third group. The first group includes the light-emitting elements E1 to E5 and the light-receiving elements D1 to D5; the second group includes the light-emitting elements E6 to E10 and the light-receiving elements D6 to D10; and the third group includes the light-emitting elements E11 to E15 and the light-receiving elements D11 to D15. The light-emitting elements of each group are aligned in a single line, and the light-receiving elements of each group are aligned in a single line. When the reflective optical sensor is in position to measure the toner density, the line of the second group is shifted by $\Delta L$ from the line of the first group in the sub-direction, and the line of the third group is shifted by $\Delta L$ from the line of the second. The distance $\Delta L$ is decided based on the velocity of the supporting member moving in the sub-direction.

The light-emitting elements E1 to E15 turn ON/OFF sequentially while the toner pattern is moving in the sub-direction at the velocity of V.

Time required for ON/OFF of the light-emitting elements E1 to E5, time required for ON/OFF of the light-emitting elements E6 to E10, and time required for ON/OFF of the light-emitting elements E11 to E15 are equal, more particularly, st/3, where st is scanning time.

The toner pattern moves by distance V·st/3 in the sub-direction in time st/3. Therefore, if $\Delta L$ is set as follows:

$$\Delta L = V \cdot st/3$$

then the spot scanning of the toner pattern by the light-emitting elements E1 to E15 is completed within the scanning time.

In the third embodiment illustrated in FIG. 4B, when the reflective optical sensor is in position to measure the toner density, the light-emitting elements E1 to E15 and the light-receiving elements D1 to D15 are aligned in a single direction that is inclined to the main-direction at an angle $\alpha$. The angle $\alpha$ is decided based on the velocity of the supporting member moving in the sub-direction.

More particularly, if the angle $\alpha$ satisfies a following Equation:

$$Z \cdot \tan\alpha = V \cdot st$$

where st is scanning time, Z is the length in the main-direction of lines on which the light-emitting elements E1 to E15 and the light-receiving elements D1 to D15 are aligned, then the spot scanning of the toner pattern by the light-emitting elements E1 to E15 is completed within the scanning time.

Figure 5:
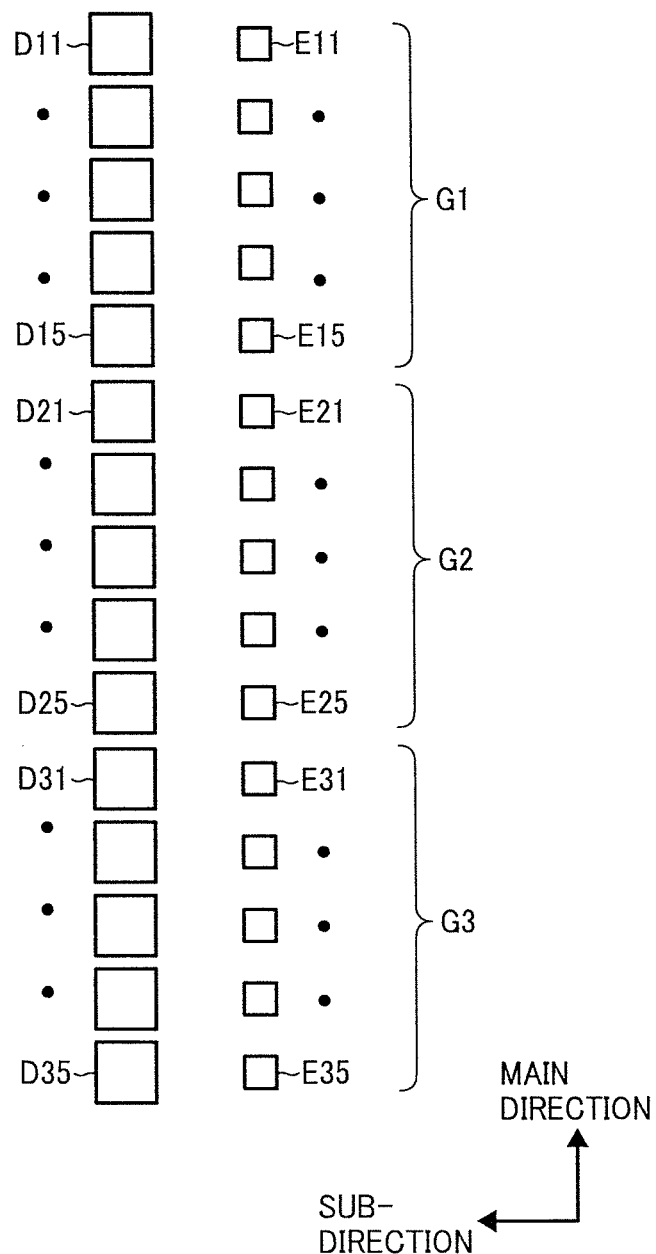
FIG. 5 is a schematic diagram of an arrangement of light-emitting elements and light-receiving in a reflective optical sensor according to a fourth embodiment of the present invention.

In a fourth embodiment of the present invention as illustrated in FIG. 5, the spot scanning is optimized as follows.

A reflective optical sensor according to the fourth embodiment includes 15 light-emitting elements and 15 light-receiving elements. The light-emitting elements correspond to the light-receiving elements, respectively in the one-to-one manner. Although the light-emitting elements and the light-receiving elements illustrated in FIG. 5 are 15, each, several tens to several hundreds of the light-emitting elements and the light-receiving elements are used in practice. To make the drawings simpler, the number of the light-emitting elements and the light-receiving elements is set to 15 in the fourth embodiment. In other words, the light-emitting elements and the light-receiving elements can be more than 15 or less than 15.

When the reflective optical sensor is in position to measure the toner density, the direction in which the 15 light-emitting elements are aligned and the direction in which the 15 light-receiving elements are aligned are substantially parallel to the main-direction.

Each of the 15 light-emitting elements makes a pair with a corresponding one of the 15 light-receiving elements. The light-emitting elements and the light-receiving elements are divided into three groups G1, G2, and G3. The groups G1, G2, and G3 are aligned in a single line extending in the main-direction.

The group G1 includes five pairs, more particularly, the light-emitting elements E11 to E15 and the light-receiving elements D11 to D15. The group G2 includes five pairs, more particularly, the light-emitting elements E21 to E25 and the light-receiving elements D21 to D25. The group G3 includes five pairs, more particularly, the light-emitting elements E31 to E35 and the light-receiving elements D31 to D35.

All the three groups G1, G2, and G3 have the same structure.

When the reflective optical sensor is in position to measure the toner density, the first light-emitting element of each group, i.e., the light-emitting elements E11, E21, and E31 turn ON/OFF simultaneously. Then, the second light-emitting element of each group, i.e., the light-emitting elements E12, E22, and E32 turn ON/OFF simultaneously. After that, the light-emitting elements E13, E23, and E33, the light-emitting elements E14, E24, and E34, and the light-emitting elements E15, E25, and E35 turn ON/OFF sequentially.

With this configuration, the scanning time can be decreased to one-third of the scanning time in the second embodiment and the third embodiment. Therefore, the spot scanning is completed while the toner pattern is passing through the scanning area.

As a variation of the fourth embodiment, it is allowable to shift the light-emitting elements and the light-receiving elements other than the light-emitting elements E11, E21, and E31 and the light-receiving elements D11, D21, and D31 in the sub-direction with the light-emitting elements E11, E21, E31 and the light-receiving elements D11, D21, D31 maintained at their respective positions illustrated in FIG. 5 in such a manner that the light-emitting elements and the light-receiving elements are aligned in a direction that is inclined to the main-direction at a certain angle. The certain angle is decided based on the velocity of the supporting member moving in the sub-direction, in the same manner as in the third embodiment.

More light-emitting elements and light-receiving elements are used in the second, the third, and the fourth embodiments as compared to the first embodiment. If the pitch is unchanged, the length of the reflective optical sensor in the main-direction, i.e., the sensing area increases. In other words, an allowable extent of the positional miss-match in the main-direction between the toner pattern and the reflective optical sensor increases. On the other hand, if the length of the reflective optical sensor is unchanged, the pitch between adjacent light-emitting elements and light-receiving elements decreases. This results in an increase in the spatial resolution in the main-direction.

As described above, M, which is the number of the light-emitting elements, can be set unequal to N, which is the number of the light-receiving elements. In fifth to seventh embodiments of the present invention illustrated in FIGS. 6A to 6C, respectively, M is not equal to N.

Figure 6A:
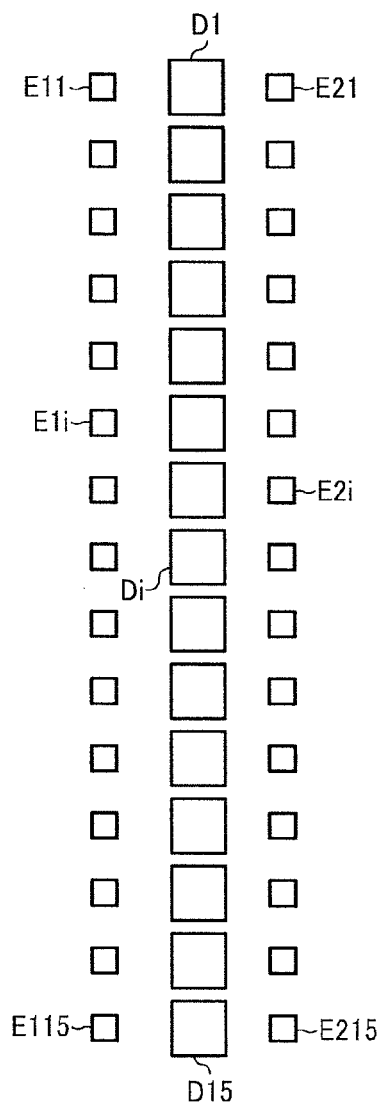
FIG. 6A is a schematic diagram of an arrangement of light-emitting elements and light-receiving in a reflective optical sensor according to a fifth embodiment of the present invention.

In the fifth embodiment illustrated in FIG. 6A, N is 15 and M is 30.

The light-emitting unit includes 15 light-emitting elements E11, ..., E1$i$ ..., and E115 that are aligned in a single line extending in the main-direction at an equal pitch, and 15 light-emitting elements E21, E2$i$ and E215 that are aligned in another single line extending in the main-direction at an equal pitch. Positions of the light-emitting elements E21, E2$i$ ..., and E215 in the main-direction are the same as positions of the light-emitting elements E11, E1i..., and E115, respectively.

The light-receiving unit includes 15 light-receiving elements D1, ..., Di..., and D15 that are aligned in a line extending in the main-direction at an equal pitch between the two lines of the light-emitting elements. Positions of the light-receiving elements D1,..., Di..., and D15 are the same in the main-direction as the positions of the light-emitting elements E11, ..., E1i..., and E115, respectively, i.e., the same in the main-direction as the positions of the light-emitting elements E21, E2i and E215, respectively.

The light-emitting elements E11 and E21, which are aligned in the same position in the main-direction, turn ON/OFF simultaneously. After that, the light-emitting elements E12 and E22 turn ON/OFF, simultaneously. The ON/OFF operation is repeated in the same manner until the light-emitting elements E115 and E215 turn ON/OFF. Thus, the output of the detection light that illuminates the supporting member and the toner pattern becomes about double.

The output of the LEDs, which are used as the light-emitting elements, in general, depends on not the light-emitting-element area but the applied current density.

If the applied current density increases, the output increases but the lifetime of the LEDs decreases. To maintain the lifetime, the applied current density be preferably lower than a certain level. If the light-emitting-element area increases (with the applied current density unchanged), the applied current amount increases. However, an increase in the light-emitting-element area results in an increase of spots for illuminating the supporting member and the toner pattern.

To solve this problem, it is preferable to double the output of the light. This has been achieved by arranging the two lines of light-emitting units, as illustrated in FIG. 6A, with both the light-emitting-element area and the current density unchanged.

Figure 6B:
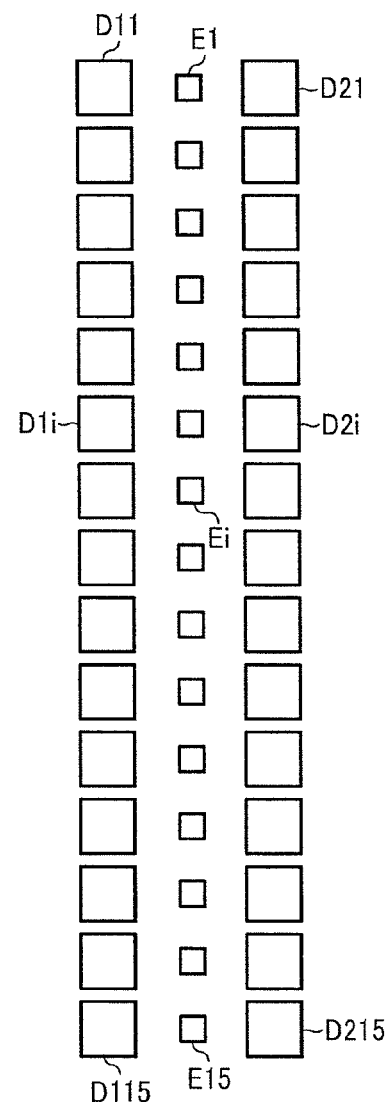
FIG. 6B is a schematic diagram of an arrangement of light-emitting elements and light-receiving in a reflective optical sensor according to a sixth embodiment of the present invention.

In the sixth embodiment illustrated in FIG. 6B, N is. 30 and M is 15.

The light-receiving unit includes 15 light-receiving elements D11, ..., D1i..., and D115 that are aligned in a single line extending in the main-direction at an equal pitch, and 15 light-receiving elements D21, D2i and D215 that are aligned in another single line extending in the main-direction at an equal pitch. The light-emitting unit includes 15 light-emitting elements E1, ..., Ei..., and E15 that are aligned in a single line extending in the main-direction at an equal pitch between the two lines of the light-receiving elements. Positions of the light-emitting element Ei, the light-receiving element D1i, and the light-receiving element D2i, where i is an arbitrary integer from 1 to 15, are the same in the main-direction.

Because PDs, which receive the detection light (reflected light), are aligned in the two lines, the light-receiving sensitivity becomes double. Alternatively, if the light-receiving-element area in the sub-direction is increased to double with the PDs being aligned in a single line, the light-receiving sensitivity increases. However, the increase in the light-receiving sensitivity is relatively small, especially when the size of the spot of the detection light reflected from the supporting member and the toner pattern is small. From the viewpoint of the improvement of the light-receiving sensitivity, it is more effective to arrange the PDs in the two lines symmetrically in the sub-direction and the LEDs between the two lines, as illustrated in FIG. 6B.

In the first to the sixth embodiments as described with reference to FIGS. 2 to 6B, the light-emitting elements and the light-receiving elements are aligned at the equal pitches, and the pitch of the light-emitting elements is equal to the pitch of the light-receiving elements. However, it is possible to set the pitch of the light-emitting elements different from the pitch of the light-receiving elements.

A seventh embodiment according to the present invention in which the pitch of the light-emitting elements different from the pitch of the light-receiving elements is described with reference to FIG. 6C. In the seventh embodiment, there are seven light-emitting elements E1, ..., Ei, ..., and E7 and 14 light-receiving elements D1, ..., Di, ..., and D14. The light-receiving elements are aligned at a pitch half of the pitch of the light-emitting elements. Each of the light-emitting elements E1 to E7 corresponds to two light-receiving elements. In this manner, the spatial resolution in the main-direction in increased by decreasing the pitch of the PDs.

If the reflective optical sensor is arranged in a line not parallel to the main-scanning direction, the higher spatial resolution in the main-direction is obtained.

Assume, more particularly, that the reflective optical sensor is arranged in such a manner that an angle between the main-scanning direction and the lines on which the light-emitting elements and the light-receiving elements are aligned is $\beta$, and the pitch of the light-emitting elements and the light-receiving elements is pt. Then, the pitch of points in the main-direction projected from the light-emitting elements and the light-receiving elements is decreased to pt·cos $\beta$, i.e., the spatial resolution increases.

In the above-described embodiments, the LEDs and the PDs are formed as the light-emitting elements and the light-receiving elements by the resin molding or by the surface mounting at an integrated and high-density manner. As described above, if extremely small LEDs and PDs dimensions of which can be adjusted in the millimeter are used, the pitch can be decreased to about 1 mm.

To increase the spatial resolution, it is necessary basically to decrease the pitch of the light-emitting elements and the light-receiving elements. In an LED array and a PD array in which LEDs and PDs are integrally arranged, the pitch is extremely small. The LED array and the PD array are used in an eighth embodiment and a ninth embodiment of the present invention.

Figure 7A:
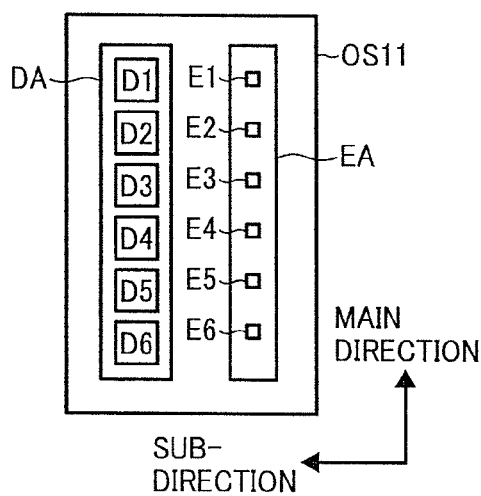
FIG. 7A is a schematic diagram of a reflective optical sensor according to an eighth embodiment of the present invention.

In the eighth embodiment illustrate in FIG. 7A, a reflective optical sensor OS11 includes an LED array (light-emitting unit) EA and a PD array (light-receiving unit) DA. The LED array EA includes six LEDs as the light-emitting elements E1 to E6 integrally aligned in a single line at an equal pitch on the same substrate. The PD array DA includes six PDs as the light-receiving elements D1 to D6 integrally aligned in a single line at an equal pitch on the same substrate. The LED array EA and the PD array DA are accommodated in the same housing of the reflective optical sensor OS11.

Figure 7B:
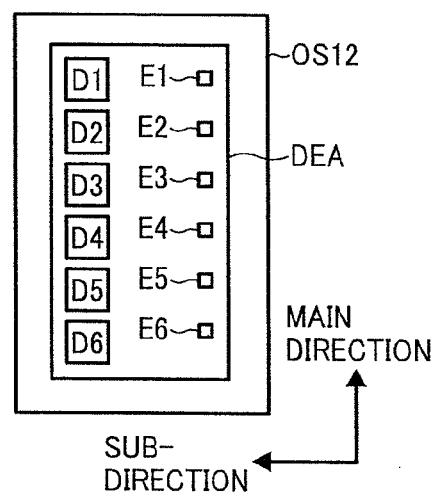
FIG. 7B is a schematic diagram of a reflective optical sensor according to a ninth embodiment of the present invention.

In the ninth embodiment illustrate in FIG. 7B, a reflective optical sensor OS12 includes a light-emitting/receiving unit array DEA. The light-emitting/receiving unit array DEA includes six LEDs as the light-emitting units E1 to E6 and six PDs as the light-receiving elements D1 to D6 arranged on the same substrate. The six LEDs are aligned in a single line at an equal pitch. The six PDs are aligned in a single line at an equal pitch. The light-emitting/receiving unit array DEA is accommodated in the same housing of the reflective optical sensor OS12.

As illustrated in FIGS. 7A and 7B, the pitch of the light-emitting elements is equal to the pitch of the light-receiving elements. A position of each light-emitting element in the main-direction is the same as a position of the corresponding light-receiving element. However, in the same manners as in the fifth to the seventh embodiments illustrated in the FIGS.

6A to 6C, the number of and the pitch of the light-emitting elements can be different from the number of and the pitch of the light-receiving elements.

To make the drawings and the description simpler, only six light-emitting elements and six light-receiving elements are illustrated in FIGS. 7A and 7B. In other words, the light-emitting elements and the light-receiving elements can be more than six or less than six.

In this manner, if the LED array and the PD array are used as the light-emitting unit and the light-receiving unit, the pitch of the light-emitting elements and the light-receiving elements can be from several tens of micrometers to several hundreds of micrometers. In other words, an extremely high spatial resolution can be obtained.

If the LED array and the PD array that are fabricated by the semiconductor processing are used instead of individual LEDs and PDs, it is possible to obtain a remarkably high positional accuracy in the light-emitting elements and the light-receiving elements.

In the ninth embodiment illustrated in FIG. 7B, because the LED array and the PD array are integrally formed on the same substrate, a relative positioning between the light-emitting elements and the light-receiving elements can be done extremely accurately.

As for the reflection properties of the toner patterns, the toner pattern in each color has different dependency to the wavelength. However, the toner pattern in each color has almost the same dependency to the near-infrared or infrared rays, especially, to rays having a wavelength within a rage from 800 nm to 1000 nm.

Therefore, the light-emitting elements in the reflective optical sensor preferably emit a light having a wavelength within the above range. Moreover, the LEDs forming the light-emitting unit preferably emit the lights having the same wavelength.

From the viewpoint of the wavelength, usage of the LED array as the light-emitting unit is preferable because the LEDs emit the lights having the same wavelength on the processing basis.

If the wavelength sensitivities of N–number of the light-receiving elements forming the light-receiving unit are different from each other, even if the light-receiving elements receive the same light reflected from the toner pattern, the outputs of the light-receiving elements differs from each other, which may cause an error in the calculation for the toner density.

Therefore, it is preferable to use PDs having the same peak sensitivity wavelength as the light-receiving elements of the light-receiving unit. From the viewpoint of the peak sensitivity wavelength, usage of the PD array as the light-receiving unit is preferable because the PDs of the PD array have the same peak sensitivity wavelength on the processing basis.

From the viewpoint of efficiency in receiving the detection light emitted from the light-emitting unit by the light-receiving unit, it is preferable to substantially match the wavelength of the detection light emitted from the LEDs forming as the light-emitting unit with the peak sensitivity wavelength of the PDs forming the light-receiving unit in an accurate manner by several tens of nanometers. A wavelength of a light emitted from a typical GaAs-based LED is about 950 nm. A peak sensitivity wavelength of a typical Si-based PD is from 800 nm to 1000 nm. Therefore, the typical GaAs-based LEDs and the typical Si-based PDs are preferable as the light-emitting elements and the light-receiving elements.

It is possible to shift the wavelength band by adjusting the compositions or the structure of the LEDs and the PDs. Thus, the wavelength of the detection light emitted from the LEDs can be set substantially matched with the peak sensitivity wavelength of the PDs.

As described above, in the reflective optical sensor, the light-emitting elements of the light-emitting unit emit the spots of the detection light onto the supporting member or the toner pattern.

If individual LEDs each integrally including a member having the lens function of collecting divergent light are used as the light-emitting elements, the LEDs form the spots of the detection light all alone.

If an LED array that does not has the lens function of collecting the detection light is used as the light-emitting unit, it is necessary to add an illumination optical system that receives the detection light from the light-emitting elements and collects and guides the detection light to the surface of the supporting member and/or a light-receiving optical system that receives the light reflected from the surface of the supporting member and collects and guides the reflected light to the light-receiving elements. By the usage of the illumination optical system and/or the light-receiving optical system, the spots of the detection light can be formed.

Even if individual LEDs having the lens function of collecting the detection light are used as the light-emitting elements, it is allowable to add the illumination optical system and/or the light-receiving optical system to form the spots of the detection light in a more efficient manner.

A tenth embodiment of the present invention is described with reference to FIGS. 8A to 8C.

Figure 8A:
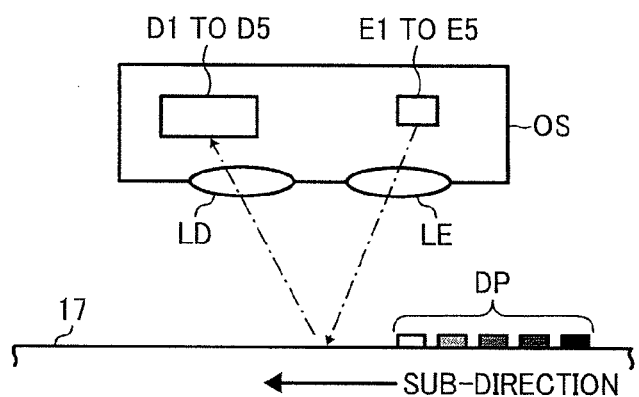
FIGS. 8A to 8C are schematic diagrams of a reflective optical sensor according to a tenth embodiment of the present invention
Figure 8B:
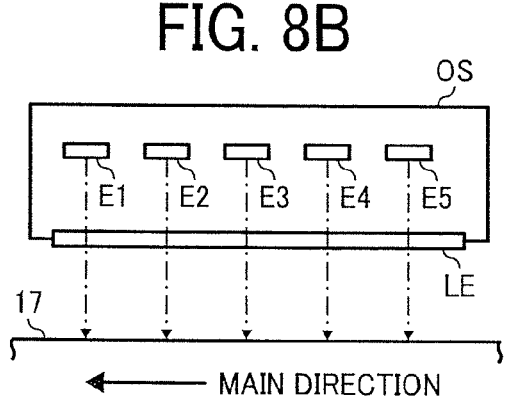

FIG. 8A is a schematic diagram of a reflective optical sensor OS according to the tenth embodiment, viewed in the main-direction.

The light-emitting unit includes five individual LEDs, as the light-emitting elements E1 to E5, aligned in a single line extending in the main-direction at an equal pitch. The light-receiving unit includes five individual PDs, as the light-receiving elements D1 to D5, aligned in a single line extending in the main-direction at an equal pitch. The LEDs as the light-emitting elements has the lens function of collecting the divergent light.

The reflective optical sensor OS includes an illumination optical system LE and a light-receiving optical system LD. The illumination optical system LE and the light-receiving optical system LD can be, as illustrated in FIGS. 8A to 8C, cylindrical lenses. The cylindrical lenses have a positive power in the sub-direction. The supporting member 17 is, more particularly, the transfer belt. A toner pattern DP is used for the toner-density measurement.

The process of measuring the toner density is performed in the same manner as described above with reference to FIGS. 2 and 3.

When the light-emitting element (LED) Ei, where i is an arbitrary integer from 1 to 5, turns ON/OFF, the detection light is collected in the sub-direction by the illumination optical system LE, and the collected detection light illuminates the supporting member 17 or the toner pattern DP. The reflected light is collected in the sub-direction by the light-receiving optical system LD, and the collected reflected light is received by the light-receiving element Di.

The illumination optical system can be used to shape the detection light so that the spot having a desired shape is formed on the supporting member or the toner pattern. The light-receiving optical system can be used to shape the reflected light so that the spot having a desired shape is formed on the light-receiving elements.

If the illumination optical system and the light-receiving optical system have the same structure, the costs for those optical systems can be suppressed. To make the drawings and the description simpler, only five light-emitting elements and five light-receiving elements are illustrated in FIGS. 8A to 8C. In other words, the light-emitting elements and the light-receiving elements can be more than five or less than five.

A reflective optical element OSA according to an eleventh embodiment of the present invention is described with reference to FIGS. 9A and 9B. The reflective optical element OSA includes the illumination optical system and the light-receiving optical system. As illustrated in FIG. 9A, the illumination optical system includes light-collecting lenses LE1 to LE5 in positions to receive the detection light from five LEDs as the light-emitting elements E1 to E5, respectively. The light-collecting lenses LEi, where i is an arbitrary integer from 1 to 5, receives the detection light as divergent light from the corresponding light-emitting element Ei, and collects the detection light. Thus, the efficiency in illumination to the supporting member 17 increases. As compared to the cylindrical lens that is used as the illumination optical system illustrated in FIGS. 8A to 8C, if lenses having the collecting power in the main-direction are used, the efficiency in the illumination increases more.

Anamorphic lenses having a power in the main-direction different from a power in the sub-direction can be used as the light-collecting lens LEi, where i is an arbitrary integer from 1 to 5.

Figure 8C:
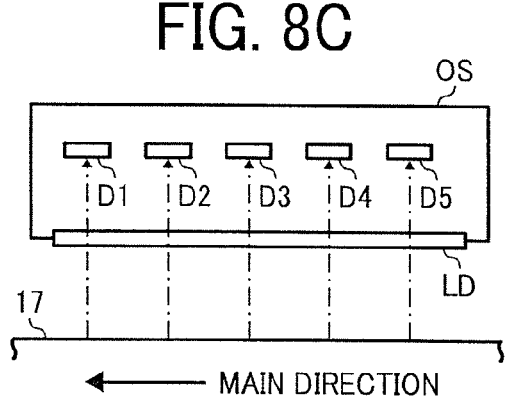
Figure 9A:
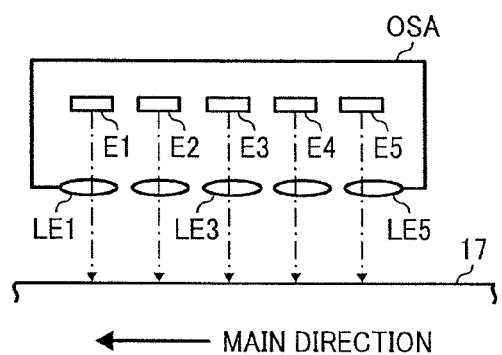
FIGS. 9A and 9B are schematic diagrams of a reflective optical sensor according to an eleventh embodiment of the present invention.
Figure 9B:
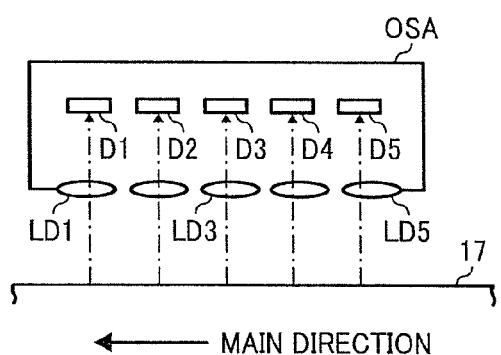

It is allowable to use the illumination optical system, which is illustrated in FIG. 9A, formed with the anamorphic lens LEi corresponding to the light-emitting element Ei in the one-to-one manner, and the light-receiving optical system, which is illustrated in FIG. 8C, formed with the cylindrical lenses having only a power in the sub-direction. A user can select a combination of a type of the illumination optical system and a type of the light-receiving optical system as appropriately, taking into consideration desired illumination efficiency, a shape of the spots of the detection light, desired light-receiving efficiency, and a shape of the spots on the light-receiving elements. To make the drawings and the description simpler, only five light-emitting elements and five light-receiving elements are illustrated in FIGS. 9A and 9B. In other words, the light-emitting elements and the light-receiving elements can be more than five or less than five.

A twelfth embodiment and a thirteenth embodiment of the present invention are described with reference to FIGS. 10A and 10B.

Figure 10A:
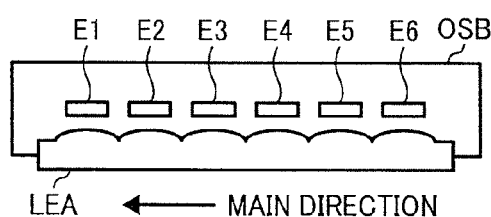
FIG. 10A is a schematic diagram of a reflective optical sensor according to a twelfth embodiment of the present invention.

In the twelfth embodiment illustrated in FIG. 10A, a reflective optical sensor OSB includes the light-emitting unit and an illumination optical system LEA. The light-emitting unit includes six LEDs as the light-emitting elements E1 to E6. The illumination optical system LEA includes convex lenses integrally arranged on a surface. The convex lenses are in positions to receive the detection light from the light-emitting elements E1 to E6, respectively and collect the received detection light.

As illustrated in FIG. 10A, although the surface facing the LEDs can collect the light, the opposite surface is flat, i.e., cannot collect the light. However, it is allowable to use surfaces that can collect the light on the both sides. Because the illumination optical system LEA is integrally formed, as compared to attaching individual lenses corresponding to the light-emitting elements, the illumination optical system LEA is easy to attach and has an advantage in the arrangement accuracy among the lens surfaces.

Although not illustrated in FIG. 10A, it is possible to use a collection of integrally-formed light-receiving lenses as the light-receiving optical system in the same manner as the light-emitting optical system.

Figure 10B:
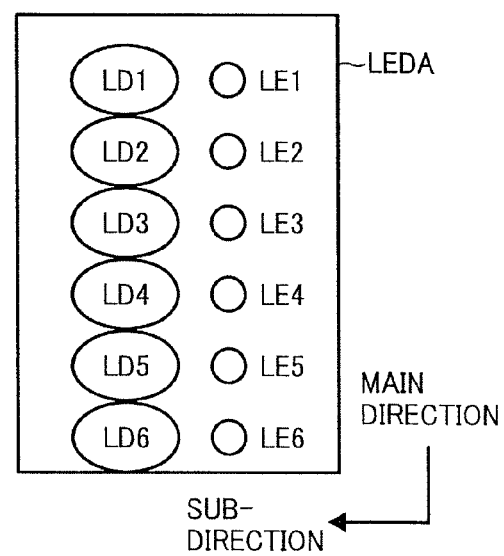
FIG. 10B is a schematic diagram of a reflective optical sensor according to a thirteenth embodiment of the present invention.

In the thirteenth embodiment illustrated in FIG. 10B, an illumination/light-receiving optical system LEDA includes six light-collecting lenses LE1 to LE6 as the illumination optical system and six light-collecting lenses LD1 to LD6 as the light-receiving optical system as a unit. Relative positions among those components are fixed, as appropriately.

Usage of the illumination/light-receiving optical system LEDA makes it possible to increase the accuracy in arrangement of the light-collecting lenses for the illumination optical system and the light-collecting lenses for the light-receiving optical system. Those light-collecting lenses can be formed on a substrate made of, for example, glass or resin at the positions as illustrated in FIG. 10B by the photolithography or the nanoimprint technology.

To make the drawings and the description simpler, six light-emitting elements and six light-receiving are elements illustrated in FIGS. 10A and 10B. In other words, the light-emitting elements and the light-receiving elements can be more than six or less than six.

If, for example, the light-emitting elements and the light-receiving elements are aligned as illustrated in FIG. 4A, 4B, 6A, 6B, or 6C, the arrangements of the illumination optical system and the light-receiving optical system are changed as appropriately based on the arrangements of the light-emitting elements and the light-receiving elements.

If the illumination optical system and the light-receiving optical system are lens arrays or lens-surface arrays, the pitch of the lenses or the lens surfaces is preferably set equal.

A toner-density measuring method according to a fourteenth embodiment of the present invention is described below.

In the reflective optical sensor that has been described with reference to FIGS. 3A to 3C, the light-emitting elements correspond to the light-receiving elements in the one-to-one manner. When any one of the light-emitting elements emits the detection light to the area out of the toner pattern of the supporting member, only the corresponding light-receiving element receives the detection light reflected from the supporting member as the specular light.

In a first example, when the light-emitting element E3 emits the detection light to the area out of the toner pattern, only the light-receiving light D3 receives the detection light and the other light-receiving elements receive no light.

On the other hand, when the light-emitting element E3 emits the detection light to the toner pattern, the detection light is diffusely reflected by the toner pattern. As a result, not only the light-receiving element D3 but also the other light-receiving elements D1, D2, D4, and D5 receive the detection light.

Figure 11A:
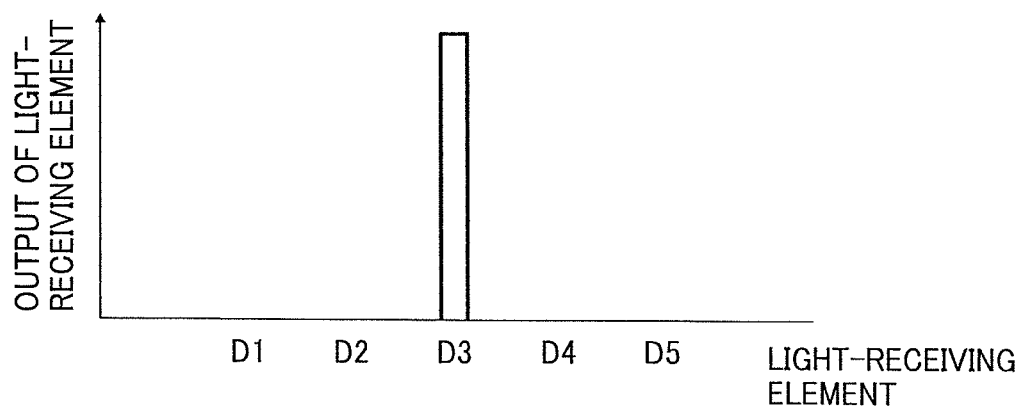
FIGS. 11A to 13C are bar charts for explaining a toner-density measuring method according to a fourteenth embodiment of the present invention.
Figure 11B:
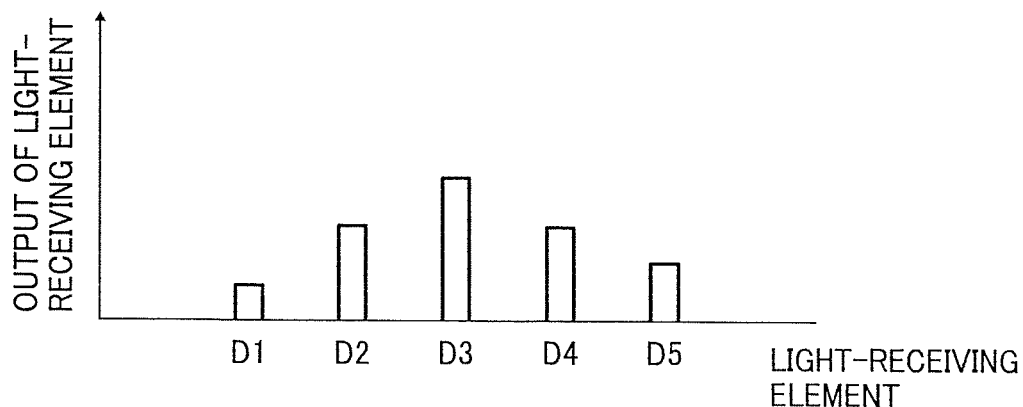

The outputs in the first example are illustrated in FIGS. 11A and 11B.

FIG. 11A is a bar chart of the outputs of the light-receiving elements D1 to D5 when the light-emitting element E3 emits the detection light to the surface of the supporting member, i.e., an area out of the toner pattern. In this case, because the detection light is specularly reflected by the area out of the toner pattern, only the light-receiving element D3 receives the detection light, and the other light-receiving elements D1, D2, D4, and D5 receive no light.

FIG. 11B is a bar chart of the outputs of the light-receiving elements D1 to D5 when the light-emitting element E3 emits the detection light to the toner pattern. In this case, because the detection light is diffusely reflected by the toner pattern, not only the light-receiving element D3 but also the other light-receiving elements D1, D2, D4, and D5 receive the detection light.

The amount of the specular reflection light is in inverse proportion to the toner density; and the amount of the diffusion reflection light is in proportion to the toner density. Therefore, the toner density of the toner pattern can be calculated from the output of the light-receiving element D3, which representing the amount of the specular reflection light, and the outputs of the other light-receiving elements D1, D2, D4, and D5 by using a predetermined algorism.

In the first example, output representing the specular reflection light (hereinafter, "specular reflection output") is clearly differentiated from output representing the diffuse reflection light (hereinafter, "diffuse reflection output"). More particularly, when the light-emitting element Di emits the detection light, the output of the corresponding light-receiving element Di is the specular reflection output, and the outputs of the non-corresponding light-receiving elements Dj, where j≠i, are the diffuse reflection output. Therefore, the algorism that is used in the toner-density calculation is simple.

However, in some embodiments of the reflective optical sensors, it is difficult to clearly differentiate the specular reflection output from the diffuse reflection output. Some outputs may be mixtures of the specular reflection output and the diffuse reflection output.

Even in the reflective optical sensor illustrated in FIGS. 3A to 3C including the five light-emitting elements E1 to E5 and the five light-receiving elements D1 to D5, if the pitch of the light-receiving elements D1 to D5 is decreased to a small value as the pitch of the light-emitting elements E1 to E5 decreases and/or if the diameter of the detection light is larger than the pitch of the light-receiving elements D1 to D5 because the detection light emitted from the light-emitting element Ei is the divergent light and the detection light, even after specularly reflected from the surface of the supporting member, goes toward the light-receiving elements in the divergence manner, the specular reflection output may disadvantageously be mixed with the diffuse reflection output.

A second example is described with the reflective optical sensor OS1 illustrated in FIGS. 3A to 3C.

As described above, the surface of the transfer belt 17 is specular. The detection light that is reflected from the area out of the toner pattern is the specular reflection light.

The light-emitting elements E1 to E5 emit the detection light, sequentially. When the light-emitting element Ei, where i is an arbitrary integer from 1 to 5, emits the detection light to the area out of the toner pattern, the corresponding light-receiving element Di and the adjacent light-receiving elements Dj, where j=i±1, receive the reflected detection light as the specular light.

Figure 12A:
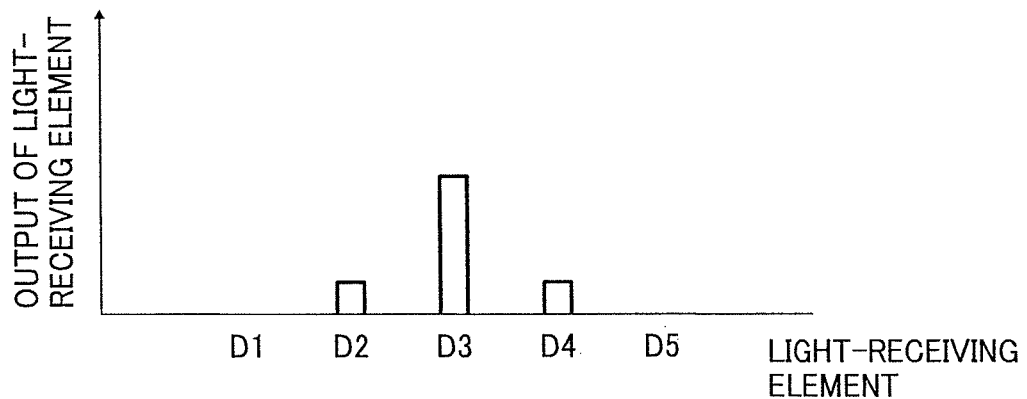

FIG. 12A is a bar chart of the outputs of the light-receiving elements D1 to D5 when the light-emitting element E3 emits the detection light to the area out of the toner pattern.

The light-receiving elements D2, D3, and D4 receive the specular reflection light from the transfer belt 17, while the outputs of the light-receiving elements D1 and D5 are zero.

Consider a case where the center of the toner pattern DP1 in the main-direction is at a position to be exposed with the spot of the detection light emitted from the light-emitting element E3, on the conditions that if the light-emitting element Ei emits the detection light to the area out of the toner pattern, the corresponding light-receiving element Di and the adjacent light-receiving elements Dj (where j=i±1) receives the reflected detection light as the specular light.

In this case, when the light-emitting element E1 emits the detection light, the detection light is specularly reflected from the surface of the transfer belt 17, and then received at the light-receiving elements D1 and D2. When the light-emitting element E2 emits the detection light, the detection light is specularly reflected from the surface of the transfer belt 17, and then received at the light-receiving elements D1, D2, and D3.

When the light-emitting element E4 emits the detection light, the detection light is specularly reflected from the surface of the transfer belt 17, and then received at the light-receiving elements D3, D4, and D5. When the light-emitting element E5 emits the detection light, the detection light is specularly reflected from the surface of the transfer belt 17, and then received at the light-receiving elements D4 and D5.

When the light-emitting element E3 emits the detection light, the detection light is specularly and diffusely reflected from the toner pattern DP1.

The amount of the specular reflection component received at each of the light-receiving elements D2, D3, and D4 decreases due to the diffuse reflection. On the other hand, the diffuse reflection light is received at not only the light-receiving element D3 but also the light-receiving elements D1, D2, D4, and D5.

Figure 12B:
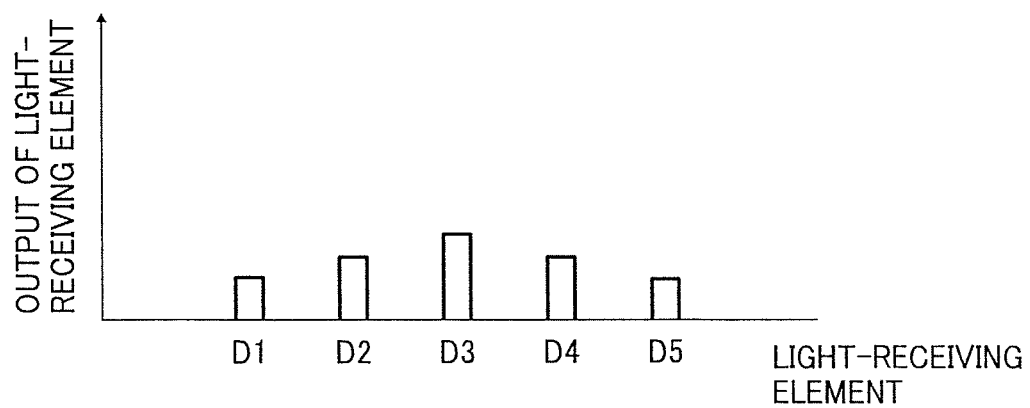

FIG. 12B is a bar chart of the outputs of the light-receiving elements D1 to D5 when the light-emitting element E3 emits the detection light to the toner pattern DP1.

It is clear from comparison of FIG. 12A with FIG. 12B, the output of the light-receiving element D3, which is corresponding to the light-emitting element E3, represents only the specular light reflected from the supporting member or the toner pattern.

The outputs of the light-receiving elements D1 and D5, which are non-corresponding to the light-emitting element E3, represent only the diffuse light reflected from the toner pattern.

The outputs of the light-receiving elements D2 and D4, which are non-corresponding to the light-emitting element E3, represent mixtures of the specular light reflected from the supporting member (FIG. 12A) and the diffuse light reflected from the toner pattern (FIG. 12B).

It is clear from comparison of FIG. 12A with FIG. 12B, the distribution of the outputs of the light-receiving elements D1 to D5 when the detection light is reflected from the surface of the supporting member differs from the distribution when the detection light is reflected from the toner pattern. Therefore, the toner density of the toner pattern can be calculated from data about the difference between those outputs.

However, from the viewpoint of simplicity of the algorism for the calculation, it is preferable to calculate the toner density from data excluding the outputs of the light-receiving elements representing the mixtures of the specular reflection component reflected from the supporting member and the diffuse reflection component reflected from the toner pattern.

In the toner-density measuring method according to the fourteenth embodiment, M−number of the light-emitting elements emit the detection light sequentially, and N−number of the light-receiving elements receive the detection light. The output of the corresponding light-receiving element is categorized to the specular reflection output, and the outputs of the non-corresponding light-receiving elements are categorized to the diffuse reflection output. Thus, the toner density is calculated from those categorized outputs.

If the toner-density measuring method is put into the above case of the light-emitting element Ei and the light-receiving element Di, where i is an arbitrary integer from 1 to 5, when the light-emitting element Ei emits the detection light, the light-receiving element Di, which receives only the specular reflection component of the detection light from the light-emitting element Ei, is assumed as the light-receiving element corresponding to the light-emitting element Ei, and the output of the light-receiving element Di is categorized to the specular reflection output.

Moreover, the light-receiving elements Dj, where j≠i and j≠i±1, are assumed as the light-receiving elements non-corresponding to the light-emitting element Ei, and the outputs of the light-receiving elements Dj are categorized to the diffuse reflection output.

When, for example, the light-emitting element E3 emits the detection light, the output of the light-receiving element D3, which is corresponding to the light-emitting element E3 is the specular reflection output, and the outputs of the light-receiving elements D1 and D5, which are non-corresponding to the light-emitting element E3, are the diffuse reflection output.

Because the light-receiving elements D2 and D4 receive both the specular reflection light and the diffuse reflection light, the outputs of the light-receiving elements D2 and D4 are categorized to neither the specular reflection output nor the diffuse reflection output.

In this manner, the outputs of the light-receiving elements D1 to D5 are categorized into three types, i.e., the specular reflection output, the diffuse reflection output, and the output neither the specular reflection output nor the diffuse reflection output. If the toner density is calculated from the specular reflection output and the diffuse reflection output only, the algorism for the calculation is simplified because the influence of the reflection from the surface of the supporting member is clearly differentiated from the influence of the reflection from the toner pattern.

An additional explanation is given for the case when the light-emitting element E3 emits the detection light. In the output of the light-receiving element D3, which is corresponding to the light-emitting element E3, the entire output is the specular reflection output, i.e., the diffuse reflection light is zero. In the outputs of the light-receiving elements D1 and D5, which are non-corresponding to the light-emitting element E3, the entire output is the diffuse reflection output, i.e., the specular light reflected from the supporting member are zero.

In most cases, the number of the light-receiving elements Dj, which are non-corresponding to the light-emitting element Ei, is two or larger. Even if the diffuse light spreads over and two or more light-receiving elements receive the diffuse light, the correct diffuse reflection output is obtained by calculating a sum of the outputs of the light-receiving elements Dj. Thus, the diffuse reflection light is detected more accurately.

For example, when the light-emitting element E3 emits the detection light to the toner pattern DP1, the output of the light-receiving element D3 is the specular reflection output and the outputs of the light-receiving elements D1 and D5 are the diffuse reflection output representing the diffuse light reflected from the toner pattern only. If the sum of the outputs of the light-receiving elements D1 and D5 is calculated and the calculated larger data is used as the diffuse reflection output, the toner density is measured more accurately.

The toner density is calculated from the outputs of the three light-receiving elements D1, D3, and D5 based on a difference between the reflection property of the supporting member (the specular reflection output, i.e., the output of the light-receiving element D3) and the reflection property of the toner pattern (the diffuse reflection output, i.e., the outputs of the light-receiving elements D1 and D5) (difference between the current specular reflection output and the reference specular reflection output and difference between the current diffuse reflection output and the reference diffuse reflection output).

The calculation is described briefly below.

It is calculated, by focusing only the specular reflection output as the reflection property, a correlation between the toner density of the toner pattern and a difference between the output of the light-receiving element D3 representing the detection light reflected from the supporting member and the output of the light-receiving element D3 representing the detection light reflected from the toner pattern. Alternatively, it is calculated, by focusing only the diffuse reflection output as the reflection property, a correlation between the toner density of the toner pattern and a difference between the sum of the outputs of the light-receiving elements D1 and D5 representing the detection light reflected from the supporting member (=0) and the sum of the outputs of the light-receiving elements D1 and D5 representing the detection light reflected from the toner pattern. Thus, the toner density is measured based on those correlations.

If both the specular reflection output and the diffuse reflection output are focused, the toner density can be calculated more accurately. In the above description, "difference" includes various meanings, of course, including "value obtained by a subtraction".

The outputs of the two light-receiving elements D2 and D4, which are not corresponding to the light-emitting element E3, are the mixtures of the specular reflection output and the diffuse reflection output, and therefore it is difficult to separate the influences of the two reflection properties. To make the algorism for calculation simpler, the toner density is calculated from data excluding the outputs of those light-receiving elements, which makes it possible to implement the more efficient processing. In the above description, it is assumed that when the light-emitting element Ei emits the detection light to the surface of the transfer belt, the corresponding light-receiving element Di and the adjacent light-receiving elements Dj (j=i±1) receive the reflected detection light as the specular light.

As described above, if a non-specular intermediate transfer belt or the like is used as the supporting member, the detection light is diffusely reflected even from the surface of the toner pattern.

However, if the reflection property of the light diffusely reflected from the supporting member is different from the reflection property of the light diffusely reflected from the toner pattern, the distribution of the outputs of the plural light-receiving elements representing the light diffusely reflected from the supporting member is different from the distribution representing the light diffusely reflected from the toner pattern. Therefore, the toner density can be measured from a difference between the distributions.

An example where the detection light is diffusely reflected from the surface of the supporting member is described below.

In the example, both M, i.e., the number of the light-emitting elements of the reflective optical sensor, and N, i.e., the number of the light-receiving elements are seven.

The conditions in this example are almost the same as the conditions in the example illustrated in FIGS. 3A to 3C except are the numbers of the light-emitting elements and the light-receiving elements are seven, and the supporting member is the non-specular intermediate transfer belt that diffusely reflects the detection light.

To make the drawing simpler, a degree of diffusion of the detection light reflected from the toner pattern is assumed larger than a degree of diffusion of the detection light reflected from the intermediate transfer belt. If the degree of diffusion of the detection light reflected from the toner pattern is smaller than the degree of diffusion of the detection light reflected from the intermediate transfer belt, the following description should be read with "intermediate transfer belt" and "toner pattern" switched.

Figure 13A:
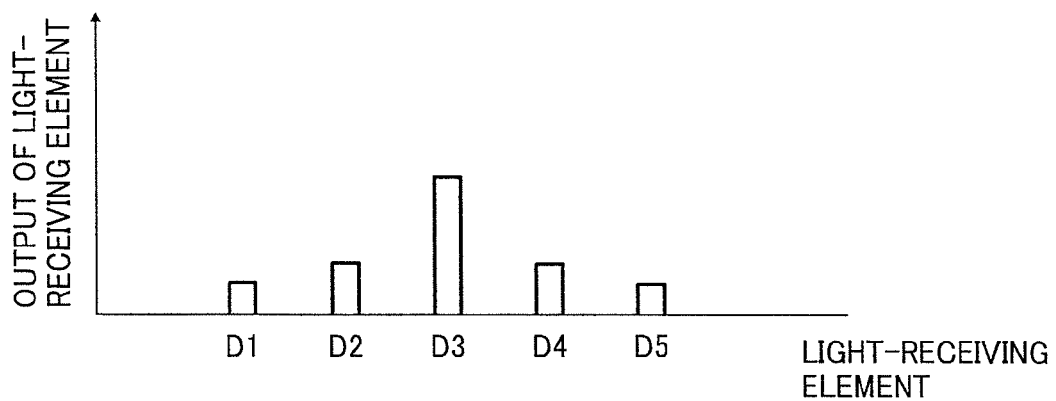

FIG. 13A is a bar chart of the outputs of the light-receiving elements D1 to D7 when the light-emitting element E4 emits the detection light to the area out of the toner pattern (intermediate transfer belt).

The light-receiving elements D2 to D6 receive the specular light and the diffuse light reflected from the intermediate transfer belt. The outputs of the light-receiving elements D1 and D7 are zero.

Figure 13B:
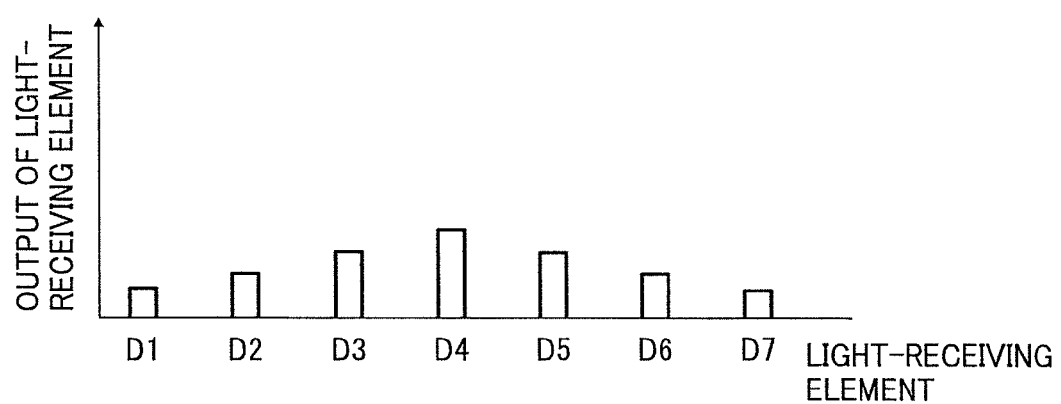

FIG. 13B is a bar chart of the outputs of the light-receiving elements D1 to D7 when the light-emitting element E4 emits the detection light to the toner pattern.

It is clear from FIG. 13B that all of the light-receiving elements D1 to D7 receive at least one of the specular light and the diffuse light reflected from the toner pattern.

Because the degree of diffusion of the detection light reflected from the toner pattern is larger than the degree of diffusion of the detection light reflected from the intermediate transfer belt, the distribution of the outputs illustrated in FIG. 13B is spreading more than the distribution of the outputs illustrated in FIG. 13A.

It is necessary to identify, from among the outputs of the light-receiving elements D2 to D6 that are larger than zero, an output including the diffuse reflection output from the bar chart of FIG. 13A. The output of the light-receiving element D4 corresponding to the light-emitting element E4 is, of course, the specular reflection output.

If it is assumed that the surface of the intermediate transfer belt is specular, it is easy to identify the light-receiving elements in positions to receive the specular reflection light through an optical simulation by using a modeled reflective optical sensor and an experiment using the actual reflective optical sensor and the transfer belt with the specular surface.

If the light-receiving elements in positions to receive the specular reflection light are identified in prior, the outputs of the light-receiving elements including the diffuse reflection light only are identifiable from among the outputs of the light-receiving elements D2 to D6 in FIG. 13A.

Figure 13C:
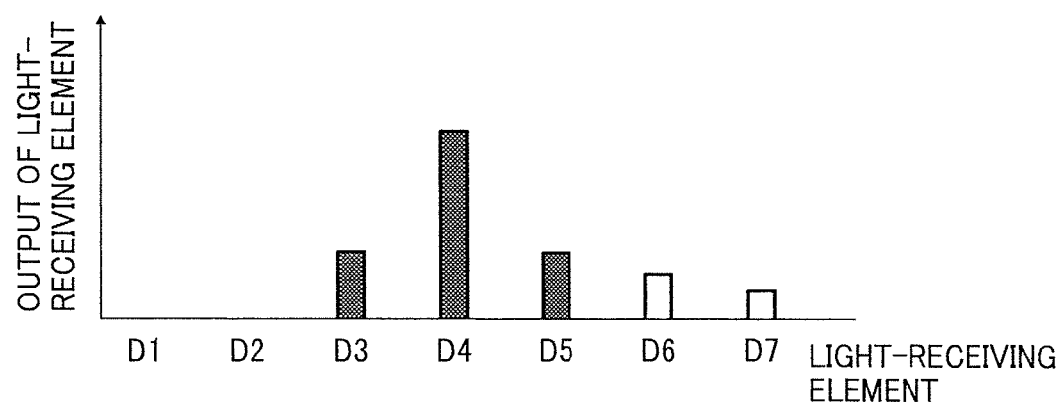

FIG. 13C is a bar chart illustrating, with hatching, the specular reflection output that is measured through the experiment using the transfer belt having the specular surface.

As compared FIG. 13C with FIG. 13A, it is clear that the output of the light-receiving element D4 illustrated in FIG. 13A is the specular reflection output representing the specular light reflected from the intermediate transfer belt, and the outputs of the light-receiving elements D2 and D6 are the diffuse reflection outputs representing the diffuse light reflected from the intermediate transfer belt.

As illustrated in FIG. 13A, the outputs of the light-receiving elements D1 and D7 are zero. This means that the outputs representing the diffuse reflection light are zero. The outputs of the light-receiving elements D3 and D5 are the mixtures of the specular reflection output and the diffuse reflection output.

It means that, in the case illustrated in FIG. 13B, the output of the light-receiving element D4 represents only the specular light reflected from the toner pattern, and the outputs of the light-receiving elements D1, D2, D6 and D7 represent only the diffuse light reflected from the toner pattern. The outputs of the light-receiving elements D3 and D5 are the mixtures of the specular reflection out and the diffuse reflection out.

In other words, the output of the light-receiving element D4, which corresponds to the light-emitting element E4, is categorized to the specular reflection output, and the outputs of the light-receiving elements D1, D2, D6 and D7, which are non-corresponding to the light-emitting element E4, are categorized to the diffuse reflection output.

The outputs of the light-receiving elements D3 and D5 are not used for the calculation for the toner density, because they are the mixtures of the specular reflection component and the diffuse reflection component.

The two cases are described above: one is described with reference to FIGS. 12A and 12B where M=N=5 and the transfer belt with the specular surface that is assumed to specularly reflect the detection light is used, and the other is described with reference to FIGS. 13A to 13C where M=N=7 and the intermediate transfer belt with the non-specular surface that is assumed to diffusely reflect the detection light is used. Those cases are exemplary, and therefore M and N can be changed to some other values and some other types of the supporting member can be used.

As illustrated in FIGS. 12A to 12B and 13A to 13C, if only the light-receiving element Di and the adjacent light-receiving element Di±1 are in positions to receive, when the light-emitting element Ei emits the detection light, the specular reflection light, the outputs of the adjacent light-receiving element Di±1 are the mixtures of the specular reflection output and the diffuse reflection output.

In this case, the number of the light-receiving elements that are in positions to receive the diffuse reflection light is N−3 (or N−2 when any of the light-emitting elements on both ends emits the detection light). It means that even if the diameter of the spot of the detection light reflected from the supporting member is larger than the pitch of the light-receiving elements because of, for example, usage of the light-emitting elements and the light-receiving elements arranged at a small pitch, only the light-receiving element Di and the adjacent light-receiving element Di±1 receive the specular light reflected from the supporting member, and therefore the number of the light-receiving elements that outputs the diffuse reflection output is at the maximum. Thus, the efficiency of detecting the diffuse reflection light is improved.

Although M is equal to N in the above cases, M can be unequal to N. Corresponding relation between the light-emitting elements and the light-receiving elements in other cases where M is unequal to N is described with reference to FIGS. 6A to 6C.

In the example illustrated in FIG. 6A, N is 15 and M is 30. The light-receiving element Di is corresponding to the light-emitting elements E1$i$ and E1$i$.

In the example illustrated in FIG. 6B, M is 15 and N is 30. The light-emitting element Ei is corresponding to the light-receiving elements D1$i$ and D2$i$.

Figure 6C:
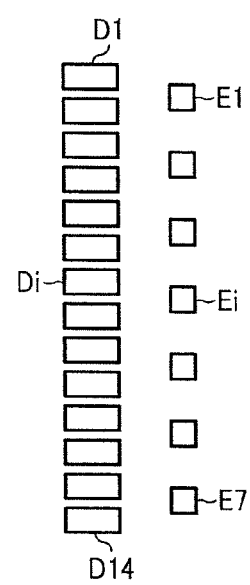
FIG. 6C is a schematic diagram of an arrangement of light-emitting elements and light-receiving in a reflective optical sensor according to a seventh embodiment of the present invention.

In the example illustrated in FIG. 6C, there are arranged the seven light-emitting elements E1, . . . , Ei, . . . , an E7 and the 14 light-receiving elements D1, . . . , Di, . . . , an D14. The light-emitting element Ei is corresponding to the light-receiving elements Dj and Dj+1, where j=2−1.

The toner-pattern positional detection is described below, where M is equal to N, and the light-receiving elements Di and Dj, where j=i±1, are positions to receive, when the light-emitting element Ei emits the detection light to the supporting member, the specular light. In the following example, the light-emitting elements E1 to EM, where M is 100, are aligned at a 100-μm pitch in the main-direction. That is, the arrangement length is 10 mm.

The light-receiving elements D1 to DN, where N is 100, are aligned at a 100-μm pitch in the main-direction. The size of the spot falling on the surface of the supporting member when the light-emitting element Ei, where i is an arbitrary integer from 1 to 100, emits the detection light is 80 μl. The width of the toner pattern in the main-direction is equal to the pitch of the light-emitting elements, i.e., 100 μm.

When the light-emitting element Ei emits the detection light, the detection light is specularly reflected from the supporting member, and is received by the light-receiving elements Di and Dj (j=i±1). The change in the output of each of the light-receiving elements D1 to D100 is checked while the light-emitting elements E1 to E100 turn ON/OFF sequentially. If the outputs of the light-receiving element Di and Di+1 (specular reflection outputs) are low when the light-emitting elements Ei and Ei+1 are ON, it is determined that the toner pattern is between the light-emitting elements Ei and Ei+1 in the main-direction.

In other words, the position of the toner pattern having the width of 100 μm in the main-direction is detected accurately by unit of 100 μm or lower.

Figure 14:
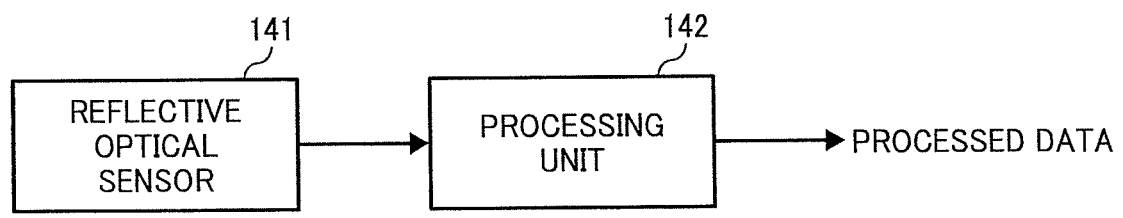
FIG. 14 is a schematic diagram of a reflective optical sensor device according to a fifteenth embodiment of the present invention.

A reflective optical sensor device according to a fifteenth embodiment of the present invention is described with reference to FIG. 14.

The reflective optical sensor device includes a reflective optical sensor 141 and a processing unit 142. The reflective optical sensor 141 can be any one of the reflective optical sensors illustrated in FIGS. 3A, 4A, 4B, 6A, 6B, 6C, 7A, 7B, etc.

The processing unit 142 categorizes the outputs of the reflective optical sensor 141. More particularly, the processing unit 142 categorizes, in the described above manner, the output of the light-receiving element corresponding to the light-emitting element in the ON state to the specular reflection output, and the output of the light-receiving element non-corresponding to the light-emitting element in the ON state to the diffuse reflection output.

According to an aspect of the present invention, there are provided a method of measuring a toner density in a novel manner, a reflective optical sensor and a reflective optical sensor device that are used in the method, an image forming apparatus that performs the method by using the reflective optical sensor and the reflective optical sensor device.

Because the toner density is measured for a short time, an operating efficiency of a main activity, i.e., image formation is improved. Moreover, an amount of toner to be consumed for the toner pattern is suppressed.

According to another aspect of the present invention, the image forming apparatus forms at least one of a mono-color image or a multi-color image, and calculates the toner density of each color.

Although the invention has been described with respect to specific embodiments for a complete and clear disclosure, the appended claims are not to be thus limited but are to be construed as embodying all modifications and alternative constructions that may occur to one skilled in the art that fairly fall within the basic teaching herein set forth.

What is claimed is:

1. A toner-density detecting method implemented on a toner image forming apparatus, the toner-density calculating method comprising:
   forming a predetermined toner pattern on a surface of a supporting member that moves in a first direction;
   emitting a detection light onto the supporting member with a light-emitting unit;
   receiving a reflected light reflected from at least one of the supporting member and the toner pattern with a light-receiving unit; and
   detecting a toner density of the toner pattern based on a difference between a reflection property of the supporting member to the detection light and a reflection property of the toner pattern to the detection light, wherein
   the light-emitting unit includes M number of light-emitting elements emitting light having the same wavelength and aligned in a third direction that is inclined to the first direction, where M is equal to or larger than three, wherein the light-emitting elements emit the detection light so that M number of light spots fall on the supporting member in such a manner that a distance between adjacent light spots in a second direction that is perpendicular to the first direction in a plane of the supporting member is equal to or smaller than a width of the toner pattern in the second direction,
   the light-receiving unit includes N number of light-receiving elements that receive the reflected light from at least one of the supporting member and the toner pattern, where N is equal to or larger than three, wherein the light-receiving elements are aligned, opposed to the supporting member, in a single direction, corresponding to the light-emitting unit, and
   the detecting includes detecting the toner density from outputs of the light-receiving elements in the light-receiving unit while causing light emitting elements in the light-emitting unit to emit light in the emitting.

2. The toner-density detecting method according to claim 1, wherein
   the toner pattern is a rectangular pattern having widths in both the first direction and the second direction, and
   the emitting includes emitting the detection light sequentially from the light-emitting elements of the light-emitting unit within a scanning time in which the toner pattern passes through an area to be exposed to the detection light in the first direction.

3. The toner-density detecting method according to claim 1, wherein
   the toner pattern is a rectangular pattern having widths in both the first direction and the second direction,
   the light-emitting unit and the light-receiving unit include P number of light-emitting/light-receiving groups each including m number of the light-emitting elements and n number of the light-receiving elements, where P is equal to or larger than two and m and n are equal to or larger than three,
   the light-emitting/light-receiving groups are arranged in a direction that is parallel to or inclined to the second direction, and
   the emitting includes emitting the detection light within a scanning time in which the toner pattern passes through an area to be exposed to the detection light in the first direction in such a manner that m sets of P number of light-emitting elements that are selected from different light-emitting/light-receiving groups are turned ON/OFF one set after another set, the P number of light-emitting elements of each set being turned ON/OFF simultaneously.

4. A reflective optical sensor for use in a toner image forming apparatus, the reflective optical sensor comprising:
   a light-emitting unit that emits a detection light onto a supporting member that moves in a first direction, the light-emitting unit including M number of light-emitting elements aligned at an angle relative to the second or main direction, where M is equal to or larger than three, the light-emitting elements turning ON/OFF individually or simultaneously and emitting light having the same wave length; and a light-receiving unit that receives a reflected light reflected from at least one of the supporting member and a toner pattern formed on the supporting member, the light-receiving unit including N number of light-receiving elements aligned at an angle relative to the second or main direction corresponding to the light-emitting unit, where N is equal to or larger than three.

5. The reflective optical sensor according to claim 4, wherein, when the reflective optical sensor is in a position to measure the toner density, the angles relative to the second or main direction are substantially parallel to a second direction that is perpendicular to the first direction in a plane of the supporting member.

6. The reflective optical sensor according to claim 4, wherein, when the reflective optical sensor is in a position to measure the toner density, each of the angles relative to the second or main direction is inclined to the second direction at a predetermined angle that is determined based on a velocity of the supporting member.

7. The reflective optical sensor according to claim 4, wherein
the light-emitting elements are aligned in a plurality of first lines that extend in the angle relative to the second or main direction, the first lines being displaced from each other in the first direction,
the light-receiving elements are aligned in a plurality of second lines extending in the angle relative to the second or main direction, the second lines being displaced from each other in the first direction, and
a distance between adjacent first lines and a distance between adjacent second lines, when the reflective optical sensor is in a position to measure the toner density, are set based on a velocity of the supporting member.

8. The reflective optical sensor according to claim 4, wherein
the light-emitting unit and the light-receiving unit include P number of light-emitting/light-receiving groups each including m number of the light-emitting elements and n number of the light-receiving elements, where P is equal to or larger than two and m and n are equal to or larger than three,
the light-emitting/light-receiving groups are arranged on one or more lines that extend along one direction, and
when measuring the toner density, m sets of P number of light-emitting elements that are selected from different light-emitting/light-receiving groups are turned ON/OFF one set after another set, the P number of light-emitting elements of each set being turned ON/OFF simultaneously.

9. The reflective optical sensor according to claim 4, wherein one light-emitting element corresponds to at least two light-receiving elements.

10. The reflective optical sensor according to claim 4, wherein one light-receiving element corresponds to at least two light-emitting elements.

11. The reflective optical sensor according to claim 4, further comprising at least one of:
an illumination optical system that guides the detection light from the light-emitting elements toward the surface of the supporting member in a convergent manner; and
a light-receiving optical system that guides the reflected light reflected from the surface of the supporting member toward the light-receiving unit in a convergent manner.

12. An image forming apparatus that forms an image with toner, the image forming apparatus comprising the reflective optical sensor according to claim 4 to calculate a toner density.

13. The image forming apparatus according to claim 12, wherein the formed image is a multicolor image or a color image and the toner density is detected for each color.

* * * * *